United States Patent
Keane, Jr. et al.

(10) Patent No.: US 11,925,731 B2
(45) Date of Patent: Mar. 12, 2024

(54) SPRAYABLE STIMULI-RESPONSIVE MICRO-HYDROGELS FOR ADHESION PREVENTION AND ENHANCED TISSUE HEALING

(71) Applicant: Texas Medical Center, Houston, TX (US)

(72) Inventors: Timothy J. Keane, Jr., Houston, TX (US); Peter Alexander Smith, Houston, TX (US); Stephen G. Ramon, Houston, TX (US)

(73) Assignee: TEXAS MEDICAL CENTER, Houston, TX (US)

(*) Notice: Subject to any disclaimer, the term of this patent is extended or adjusted under 35 U.S.C. 154(b) by 0 days.

(21) Appl. No.: 17/896,525

(22) Filed: Aug. 26, 2022

(65) Prior Publication Data

US 2022/0401631 A1    Dec. 22, 2022

Related U.S. Application Data

(63) Continuation of application No. PCT/US2021/020028, filed on Feb. 26, 2021.

(60) Provisional application No. 62/983,520, filed on Feb. 28, 2020.

(51) Int. Cl.
*A61L 31/14* (2006.01)
*A61L 31/00* (2006.01)
*A61L 31/04* (2006.01)

(52) U.S. Cl.
CPC ........... *A61L 31/145* (2013.01); *A61L 31/005* (2013.01); *A61L 31/041* (2013.01); *A61L 2400/06* (2013.01)

(58) Field of Classification Search
None
See application file for complete search history.

(56) References Cited

U.S. PATENT DOCUMENTS

| | | |
|---|---|---|
| 6,629,774 B1 | 10/2003 | Gruendeman |
| 6,974,796 B1 | 12/2005 | Girsh |
| 7,575,131 B2 | 8/2009 | Feinberg et al. |
| 8,172,010 B2 | 5/2012 | Strachan |
| 8,361,503 B2 | 1/2013 | Badylak et al. |
| 8,691,276 B2 | 4/2014 | Badylak et al. |
| 8,716,438 B2 | 5/2014 | Agrawal et al. |
| 8,741,352 B2 | 6/2014 | Hodde et al. |
| 8,874,204 B2 | 10/2014 | Sih et al. |
| 9,034,357 B2 | 5/2015 | Stopek |
| 9,259,694 B2 | 2/2016 | Hanada |
| 9,340,602 B2 | 5/2016 | Agrawal et al. |
| 9,498,271 B2 | 11/2016 | Osborne et al. |
| 9,757,495 B2 | 9/2017 | Murray |
| 10,092,676 B2 | 10/2018 | Amoroso et al. |
| 10,456,501 B2 | 10/2019 | Christman et al. |
| 10,471,182 B2 | 11/2019 | Hiles et al. |
| 2006/0251702 A1 | 11/2006 | Janis et al. |
| 2012/0083828 A1 | 4/2012 | Wheeler et al. |
| 2012/0251507 A1* | 10/2012 | Matheny ............. A61L 27/3633 424/572 |
| 2013/0251687 A1 | 9/2013 | Christman et al. |
| 2015/0010510 A1* | 1/2015 | Badylak ................. A61K 35/32 424/549 |
| 2018/0126037 A1 | 5/2018 | Huh et al. |
| 2018/0303970 A1 | 10/2018 | Sumitran-Holgersson |
| 2018/0353648 A1 | 12/2018 | Jung et al. |
| 2019/0038803 A1 | 2/2019 | Badylak et al. |
| 2019/0060521 A1 | 2/2019 | Badylak et al. |
| 2019/0117837 A1 | 4/2019 | Badylak et al. |
| 2019/0184060 A1* | 6/2019 | Bulman ................. A61P 41/00 |
| 2019/0374683 A1 | 12/2019 | Badylak et al. |
| 2020/0009187 A1* | 1/2020 | Badylak .................... A61P 1/04 |
| 2023/0372615 A1 | 11/2023 | Smith et al. |

FOREIGN PATENT DOCUMENTS

| | | |
|---|---|---|
| WO | WO-03063923 A1 | 8/2003 |
| WO | WO-2008106613 A2 | 9/2008 |
| WO | WO-2015143310 A1 | 9/2015 |
| WO | WO-2017024193 A1 * | 2/2017 |
| WO | WO-2018161028 A1 | 9/2018 |

(Continued)

OTHER PUBLICATIONS

Keane TJ, Horejs CM, Stevens MM. Scarring vs. functional healing: Matrix-based strategies to regulate tissue repair. Adv Drug Deliv Rev. Apr. 2018;129:407-419. Epub Feb. 6, 2018.
PCT/US2021/020028 International Search Report and Written Opinion dated Jun. 18, 2021.
Sawkins MJ et al. Hydrogels derived from demineralized and decellularized bone extracellular matrix. Acta Biomater. Aug. 2013;9(8):7865-73. Epub Apr. 25, 2013.
PCT/US2021/061216 International Search Report and Written Opinion dated Feb. 10, 2022.
Shinjo, J. et al., Simulation of liquid jet primary breakup: Dynamics of ligament and droplet formation, International Journal of Multiphase Flow 36:513-532 (2010).
Co-pending U.S. Appl. No. 18/409,605, inventors Keane, Jr.; Timothy J. et al., filed Jan. 10, 2024.

*Primary Examiner* — Robert A Wax
*Assistant Examiner* — William Craigo
(74) *Attorney, Agent, or Firm* — Wilson Sonsini Goodrich & Rosati

(57) ABSTRACT

Provided are methods, devices and compositions for reducing and/or inhibiting postsurgical tissue adhesion using a hydrogel film disposed onto a target tissue, thereby providing an adhesion barrier that remains over said target tissue for a prescribed period of time. In some embodiments, the hydrogel film is formed by the gelation of a pre-gel mixture applied onto the target tissue as a plurality of particles having an average maximum dimension, such as diameter, of at most about 500 μm. In some embodiments, the hydrogel film has a minimum storage modulus of 100 Pa. In some embodiments, the pre-gel mixture comprises an ECM digest having a collagen to carbohydrate ratio (by mass) of at least 70:1.

17 Claims, 7 Drawing Sheets

(56) References Cited

FOREIGN PATENT DOCUMENTS

| WO | WO-2019213482 A1 | 11/2019 |
|----|------------------|---------|
| WO | WO-2021174085 A1 | 9/2021  |
| WO | WO-2022115788 A1 | 6/2022  |

* cited by examiner

SPRAYABLE STIMULI-RESPONSIVE MICRO-HYDROGELS FOR ADHESION PREVENTION AND ENHANCED TISSUE HEALING

CROSS-REFERENCE

This application is a continuation of International Application No.: PCT/US2021/020028, filed Feb. 26, 2021, which claims the benefit of U.S. Provisional Application No. 62/983,520, filed Feb. 28, 2020, which are incorporated by reference herein in their entirety.

BACKGROUND

Surgical procedures involving certain internal organs can result in complications due to the formation of tissue adhesions between adjacent organs. For example, peritoneal adhesions are fibrous tissues that tether organs to one another or to the peritoneum and are a significant cause of post-surgical morbidity. Peritoneal adhesions can have long term health effects, wherein small bowel obstruction, infertility, chronic abdominal and pelvic pain, and difficult re-operative surgery are among the most common consequences of adhesions. In another example, post-operative complication related to colorectal procedures are frequent and the occurrence of small bowel obstruction is a significant risk. For example, an estimated 9% of colorectal patients suffer from small bowel obstruction following colorectal procedures. Moreover, the occurrence of small bowel obstruction due to tissue adhesion occurs at an estimated 2.4% with any abdominal pelvic surgery, resulting in an average length of hospital stay of about 8 days, and in hospital mortality of about 2.5%.

As such, there is a need for improved devices and hydrogels for reducing and/or inhibiting postsurgical tissue adhesion.

SUMMARY

Provided herein are methods, devices and compositions for reducing and/or inhibiting postsurgical tissue adhesion using a hydrogel film disposed onto a target tissue, thereby providing an adhesion barrier that remains over said target tissue for a prescribed period of time Disclosed herein, in some embodiments, is a method for reducing postsurgical tissue adhesion and/or scarring at a target tissue, comprising: a) forming particles of a pre-gel mixture comprising an ECM digest and a buffer solution, wherein the ECM digest comprises a collagen to carbohydrate ratio of at least about 70:1, wherein the buffer solution promotes a phase change of the pre-gel mixture to a hydrogel, wherein the particles of the pre-gel mixture have an average maximum dimension of at most 500 μm; b) applying the particles of the pre-gel mixture to a target tissue; and c) promoting the formation of the hydrogel by 1) increasing a temperature of the pre-gel mixture by presenting the pre-gel mixture to the target tissue at a temperature that is lower than a temperature of the target tissue, 2) increasing a temperature of the pre-gel mixture by heating the pre-gel mixture, 3) exposing the pre-gel mixture to a light source; 4) interacting a chemical with the pre-gel mixture; 5) interacting an enzyme with the particles of the pre-gel mixture; or 6) a combination thereof, wherein the hydrogel forms a hydrogel film over the target tissue, and wherein the hydrogel film is at least 10 μm thick and comprises a storage modulus of at least 100 Pa.

Disclosed herein, in some embodiments, is a method for reducing postsurgical tissue adhesion and/or scarring, the method comprising: applying a plurality of particles of a pre-gel mixture onto a target tissue, wherein the plurality of particles have an average maximum dimension of at most 500 μm, the pre-gel mixture comprising an extracellular matrix (ECM) digest having a collagen to carbohydrate ratio of at least about 70:1, wherein the target tissue and/or environment about the target tissue promote gelation of the pre-gel mixture to form a hydrogel film having a storage modulus of at least about 100 Pa.

Disclosed herein, in some embodiments, is a method for reducing postsurgical tissue adhesion and/or scarring, the method comprising: applying a plurality of particles of a pre-gel mixture onto a target tissue, wherein the plurality of particles have an average maximum dimension of at most 500 μm, the pre-gel mixture comprising an extracellular matrix (ECM) digest, wherein the target tissue and/or environment about the target tissue promotes gelation of the pre-gel mixture to form a hydrogel film having a storage modulus of at least about 100 Pa.

Disclosed herein, in some embodiments, is a method for reducing postsurgical tissue adhesion and/or scarring, the method comprising: applying a plurality of particles of a pre-gel mixture onto a target tissue, wherein the plurality of particles have an average maximum dimension of at most 500, the pre-gel mixture comprising an extracellular matrix (ECM) digest having a collagen to carbohydrate ratio of at least about 70:1, wherein the target tissue and/or environment about the target tissue promotes gelation of the pre-gel mixture to form a hydrogel film.

Disclosed herein, in some embodiments, is a method for reducing postsurgical tissue adhesion and/or scarring, the method comprising: a) forming a plurality of particles of a pre-gel mixture, wherein the plurality of particles have an average maximum dimension of at most 500 μm, the pre-gel mixture comprising an extracellular matrix (ECM) digest having a collagen to carbohydrate ratio of at least about 70:1; and b) applying the pre-gel mixture onto a target tissue, wherein the target tissue and/or environment about the target tissue promotes gelation of the pre-gel mixture to form a hydrogel film having a storage modulus of at least about 100 Pa.

Disclosed herein, in some embodiments, is a method for reducing postsurgical tissue adhesion and/or scarring, the method comprising: a) forming a plurality of particles of a pre-gel mixture, wherein the plurality of particles have an average maximum dimension of at most 500 μm, the pre-gel mixture comprising an extracellular matrix (ECM) digest having a collagen to carbohydrate ratio of at least about 70:1; and b) applying the pre-gel mixture onto a target tissue, wherein the target tissue and/or environment about the target tissue promotes gelation of the pre-gel mixture to form a hydrogel film.

Disclosed herein, in some embodiments, is a method for reducing postsurgical tissue adhesion and/or scarring, the method comprising: a) forming a plurality of particles of a pre-gel mixture, wherein the plurality of particles have an average maximum dimension of at most 500 μm, the pre-gel mixture comprising an extracellular matrix (ECM) digest; and b) applying the pre-gel mixture onto a target tissue, wherein the target tissue and/or environment about the target tissue promotes gelation of the pre-gel mixture to form a hydrogel film having a storage modulus of at least about 100 Pa.

In some embodiments, for any method disclosed herein, the collagen to carbohydrate ratio is from about 70:1 to about 400:1. In some embodiments, for any method disclosed herein, the carbohydrate comprises glycosaminoglycans. In some embodiments, for any method disclosed herein, the collagen to carbohydrate ratio comprises a ratio of a mass (e.g., micrograms) of the collagen in the ECM digest to a mass (e.g., micrograms) of the carbohydrate in the ECM digest. In some embodiments, for any method disclosed herein, applying the pre-gel mixture comprises spraying the pre-gel mixture onto the target tissue. In some embodiments, for any method disclosed herein, the pre-gel mixture is sprayed uniformly onto the target tissue. In some embodiments, for any method disclosed herein, the hydrogel film covers at least a portion of the target tissue. In some embodiments, for any method disclosed herein, the hydrogel film is configured to adhere to the target tissue upon gelation. In some embodiments, for any method disclosed herein, at least one of the plurality of particles has an maximum dimension of at most 300 µm. In some embodiments, for any method disclosed herein, at least one of the plurality of particles has a maximum dimension of about 30-250 µm. In some embodiments, for any method disclosed herein, the plurality of particles have an average maximum dimension of about 300 µm. In some embodiments, for any method disclosed herein, the hydrogel film has a storage modulus of at least about 200 Pa. In some embodiments, for any method disclosed herein, the hydrogel film has a thickness of at least about 15 µm. In some embodiments, for any method disclosed herein, the hydrogel film has a thickness from about 10 µm to about 5 mm. In some embodiments, for any method disclosed herein, the ECM digest comprises bone ECM. In some embodiments, for any method disclosed herein, the hydrogel film is configured to substantially or completely degrade at least 3 days after being formed. In some embodiments, for any method disclosed herein, the hydrogel film is configured to substantially or completely degrade at least 6 days after being formed. In some embodiments, for any method disclosed herein, the hydrogel film is configured to adhere to the target tissue for at least 3 days after being formed. In some embodiments, for any method disclosed herein, the hydrogel film is configured to adhere to the target tissue for at least 6 days after being formed. In some embodiments, for any method disclosed herein, the target tissue and/or environment surrounding the target tissue causes gelation of the pre-gel mixture less than 5 seconds after being applied onto the target tissue. In some embodiments, for any method disclosed herein, the target tissue and/or environment surrounding the target tissue provides enable the promoting the formation of the hydrogel. In some embodiments, for any method disclosed herein, the temperature of the target tissue is at least about 25° C., at least about 30° C., or at least about 35° C. In some embodiments, for any method disclosed herein, the promoting the formation of the hydrogel comprises exposing the pre-gel mixture to a light source, wherein the pre-gel mixture comprises a photoinitiator, photosensitizer, and/or light-reactive polymer, so as to cause gelation of the pre-gel mixture upon exposure to said light source. In some embodiments, for any method disclosed herein, the pre-gel mixture is applied onto the target tissue using a device located a prescribed distance from the target tissue. In some embodiments, for any method disclosed herein, the pre-gel mixture is applied onto the target tissue once a prescribed time after completion of a surgical procedure has lapsed. In some embodiments, for any method disclosed herein, the target tissue is peritoneal, abdominal, pelvic, spinal, orthopedic, nasal, or any combination thereof. In some embodiments, for any method disclosed herein, the plurality of particles comprises a plurality of droplets. In some embodiments, for any method disclosed herein, the maximum dimension is a maximum diameter. In some embodiments, for any method disclosed herein, the average maximum dimension refers to an average of the maximum dimension for all the plurality of particles. In some embodiments, for any method disclosed herein, the carbohydrate comprises glycosaminoglycans. In some embodiments, for any method disclosed herein, a viscosity of the pre-gel mixture is reduced upon being subject to shear stress. In some embodiments, for any method disclosed herein, the viscosity of the pre-gel mixtures is reduced from about 1,000 cP to about 100 cP, when increasing an applied shear rate on the pre-gel mixture from about 0.1 s$^{-1}$ to about 1,000 s$^{-1}$. In some embodiments, for any method disclosed herein, the viscosity of the pre-gel mixtures is reduced from about 500,000 Pa to about 100 Pa. In some embodiments, for any method disclosed herein, the viscosity of the pre-gel mixtures is reduced from about 500,000 Pa to about 1,000 Pa.

Disclosed herein, in some embodiments, is a spray particle for reducing postsurgical tissue adhesion and/or scarring, the spray particle having an average maximum dimension of at most 500 µm and comprising: a pre-gel mixture comprising an extracellular matrix (ECM) digest having a collagen to carbohydrate ratio of at least about 70:1, wherein the pre-gel ECM mixture is configured to gel upon being applied onto a target tissue to form a hydrogel, the hydrogel having a storage modulus of at least about 100 Pa.

Disclosed herein, in some embodiments, is a spray particle for reducing postsurgical tissue adhesion and/or scarring, the spray particle having an average maximum dimension of at most 500 µm and comprising: a pre-gel mixture comprising an extracellular matrix (ECM), wherein the pre-gel mixture is configured to gel upon being applied onto a target tissue to form a hydrogel, the hydrogel having a storage modulus of at least about 100 Pa.

Disclosed herein, in some embodiments, is a spray particle for reducing postsurgical tissue adhesion and/or scarring, the spray particle having an average maximum dimension of at most 500 µm and comprising: a pre-gel ECM mixture comprising an extracellular matrix (ECM) digest having a collagen to carbohydrate ratio of at least about 70:1, wherein the pre-gel ECM mixture is configured to gel upon being disposed onto a target tissue to form a hydrogel.

In some embodiments, for any spray particle disclosed herein, the collagen to carbohydrate ratio is from about 70:1 to about 400:1. In some embodiments, for any spray particle disclosed herein, the spray particle has a maximum dimension of about 250 µm. In some embodiments, for any spray particle disclosed herein, the spray particle has a maximum dimension of about 30-100 µm. In some embodiments, for any spray particle disclosed herein, the hydrogel has a storage modulus of at least about 500 Pa. In some embodiments, for any spray particle disclosed herein, the hydrogel has a storage modulus of at least about 250 Pa. In some embodiments, for any spray particle disclosed herein, the ECM digest comprises bone ECM. In some embodiments, for any spray particle disclosed herein, the spray particle is a droplet. In some embodiments, for any spray particle disclosed herein, the maximum dimension is a diameter.

Disclosed herein, in some embodiments, is a hydrogel for reducing postsurgical tissue adhesion and/or scarring, the hydrogel comprising: a coating of gelled pre-gel mixture applied onto a target tissue, the pre-gel mixture comprising an extracellular matrix (ECM) digest having a collagen to carbohydrate ratio of at least about 70:1, the hydrogel having a storage modulus of at least about 100 Pa, the hydrogel forming a hydrogel film on the target tissue and having a thickness less than 5 mm, the hydrogel film configured to adhere to the target tissue for at least about 3 days.

Disclosed herein, in some embodiments, is a hydrogel for reducing postsurgical tissue adhesion and/or scarring, the hydrogel comprising: an extracellular matrix (ECM) having a collagen to carbohydrate ratio of at least about 70:1, the hydrogel having a storage modulus of at least about 100 Pa, the hydrogel forming a hydrogel film on the target tissue and having a thickness of less than 5 mm, the hydrogel film configured to adhere to a target tissue for at least about 3 days.

In some embodiments, for any hydrogel disclosed herein, the collagen to carbohydrate ratio is from about 70:1 to about 400:1. In some embodiments, for any hydrogel film disclosed herein, the hydrogel film having a thickness less than 5 mm, the hydrogel film configured to adhere to the target tissue for at least about 5 days. In some embodiments, for any hydrogel film disclosed herein, the hydrogel film covers at least a portion of the target tissue. In some embodiments, for any hydrogel film disclosed herein, the hydrogel film has a storage modulus of at least about 100 Pa. In some embodiments, for any hydrogel film disclosed herein, the hydrogel film has a thickness of at least about 10 µm. In some embodiments, for any hydrogel film disclosed herein, the hydrogel film has a thickness of about 30 µm to about 5 mm. In some embodiments, for any hydrogel film disclosed herein, the ECM digest comprises bone ECM.

Disclosed herein, in some embodiments, is a device for reducing postsurgical tissue adhesion and/or scarring; the device comprising: a) an extracellular matrix (ECM) digest having a collagen to carbohydrate ratio of at least about 70:1, b) a gel promoter solution, and c) a device body containing the ECM digest and gel promoter solution, the device body configured to combine the ECM digest and gel promoter solution to form a pre-gel mixture, the device body configured to deliver the pre-gel mixture onto a target tissue as a plurality of particles, wherein the plurality of particles have an average maximum dimension of at most 500 µm, wherein the target tissue and/or an environment about the target tissue promotes gelation of the pre-gel mixture to form a hydrogel having a storage modulus of at least about 100 Pa.

Disclosed herein, in some embodiments, is a device for reducing postsurgical tissue adhesion and/or scarring; the device comprising: a) a pre-gel mixture comprising an extracellular matrix (ECM); and b) a device body containing the pre-gel mixture, the device body configured to deliver the pre-gel mixture onto a target tissue as a plurality of particles having an average maximum dimension of at most 500 µm, wherein the target tissue and/or environment about the target tissue promotes gelation of the pre-gel mixture to form a hydrogel film having a storage modulus of at least about 100 Pa.

Disclosed herein, in some embodiments, is a device for reducing postsurgical tissue adhesion and/or scarring; the device comprising: a) a pre-gel mixture comprising an extracellular matrix (ECM) digest having a collagen to carbohydrate ratio of at least about 70:1; and b) a device body containing the pre-gel mixture, the body configured to deliver the pre-gel mixture onto a targeted tissue as a plurality of particles having an average maximum dimension of at most 500 µm, wherein the target tissue and/or environment about the target tissue promotes gelation of the pre-gel mixture to form a hydrogel film.

In some embodiments, for any device disclosed herein, the device further comprises an attachment configured to couple with the device body, wherein the pre-gel mixture is reduced to the plurality of particles by passing through said attachment. In some embodiments, for any device disclosed herein, the attachment is configured to deliver the plurality of particles onto the target tissue. In some embodiments, for any device disclosed herein, the attachment is an atomizer. In some embodiments, for any device disclosed herein, the device body is a spray nozzle, diffuser, or aerosolizer. In some embodiments, for any device disclosed herein, the device body is a spray catheter. In some embodiments, for any device disclosed herein, the device body is a syringe. In some embodiments, for any device disclosed herein, the device body comprises an inlet configured to receive the pre-gel mixture, and an outlet configured to deliver the pre-gel mixture. In some embodiments, for any device disclosed herein, the device body comprises a channel disposed between the inlet and outlet. In some embodiments, for any device disclosed herein, the attachment is configured to couple to the outlet. In some embodiments, for any device disclosed herein, the delivering the pre-gel mixture comprises spraying the pre-gel mixture onto the target tissue. In some embodiments, for any device disclosed herein, the device is configured to spray the pre-gel mixture uniformly onto the target tissue. In some embodiments, for any device disclosed herein, the hydrogel film is configured to adhere to the target tissue upon gelation. In some embodiments, for any device disclosed herein, at least one of the plurality of particles has a maximum dimension of about 250 µm. In some embodiments, for any device disclosed herein, at least one of the plurality of particles has a maximum dimension of about 30-100 µm. In some embodiments, for any device disclosed herein, the hydrogel film has a storage modulus of at least about 100 Pa. In some embodiments, for any device disclosed herein, the hydrogel film has a thickness of at least about 5 µm or 10 µm. In some embodiments, for any device disclosed herein, the ECM digest comprises bone ECM. In some embodiments, for any device disclosed herein, the plurality of particles is a plurality of droplets. In some embodiments, for any device disclosed herein, the maximum dimension is a diameter. In some embodiments, for any device disclosed herein, the device is configured to aerosolize the pre-gel mixture. In some embodiments, for any device disclosed herein, the device is further configured to reduce a viscosity of the pre-gel mixture prior to or upon delivery to the target tissue. In some embodiments, for any device disclosed herein, the viscosity of the pre-gel mixture is reduced from 1000 cP to 100 cP. In some embodiments, for any device disclosed herein, the viscosity of the pre-gel mixture is reduced from about 500,000 Pa to about 100 Pa.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
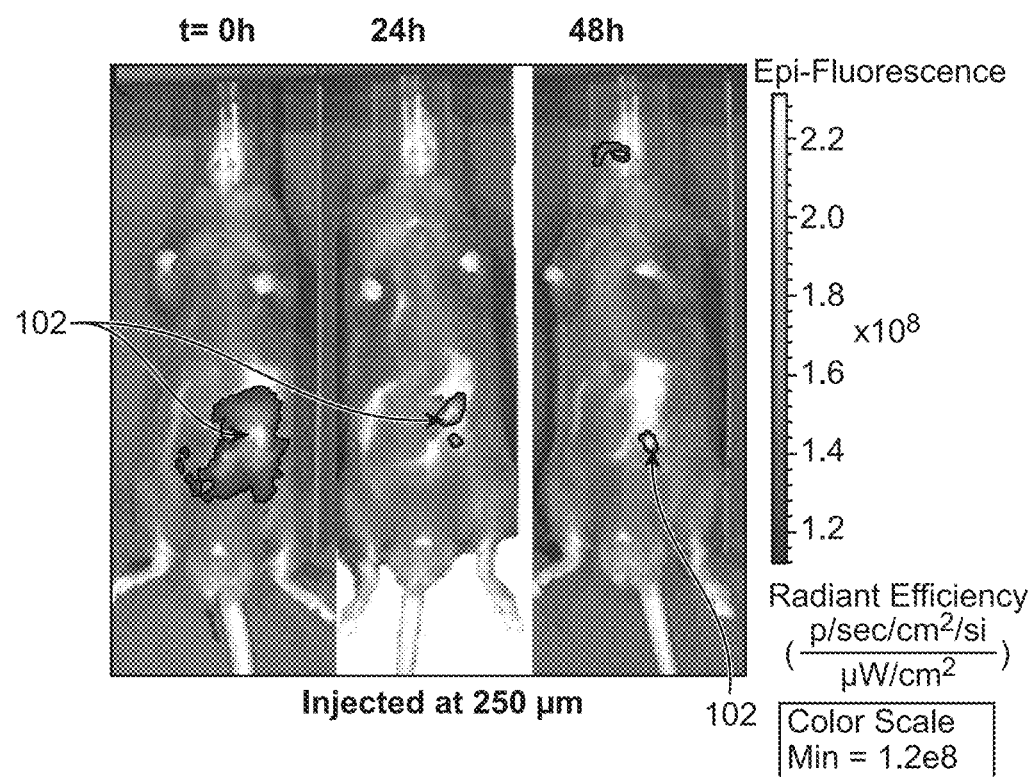
FIG. 1A depicts an image of hydrogel film retention on peritoneal issue over 2 days, wherein the hydrogel film was formed from ECM mixture particles having an average diameter of at most 250 µm.

Postsurgical tissue adhesion is a common complication causing discomfort and long term health effects for patients. In some cases, patients are monitored for several days following a surgical procedure to identify and mitigate complications arising due to tissue adhesion. Disclosed herein are methods, devices and compositions for reducing and/or inhibiting postsurgical tissue adhesion and/or scarring using a hydrogel film disposed onto a target tissue, thereby providing an adhesion barrier that remains over said target tissue for a prescribed period of time. In some embodiments, the hydrogel film is formed by the gelation of a pre-gel mixture sprayed onto the target tissue as a plurality of particles having an average maximum dimension, such as diameter, of at most about 500 μm. In some embodiments, the hydrogel film has a minimum storage modulus of 250 Pa. In some embodiments, the pre-gel mixture comprises an ECM digest having a collagen to carbohydrate ratio of at least about 70:1. In some embodiments, the carbohydrate comprises glycosaminoglycans.

Disclosed herein, in certain embodiments, are methods, devices and compositions for reducing and/or inhibiting postsurgical tissue adhesion and/or scarring using an ECM based hydrogel film having a storage modulus of at least 250 Pa. Disclosed herein, in certain embodiments, are methods, devices and compositions for reducing and/or inhibiting postsurgical tissue adhesion and/or scarring using an ECM-based hydrogel film formed with a crosslinking agent to achieve a storage modulus of at least 250 Pa. Disclosed herein, in certain embodiments, are methods, devices and compositions for reducing and/or inhibiting postsurgical tissue adhesion and/or scarring using a synthetic hydrogel film formed with synthetic and naturally derived materials to achieve a storage modulus of at least 250 Pa.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The term "in vivo" is used to describe an event that takes place in a subject's body.

The term "target tissue" is used to describe a tissue for which protection against adhesion with surrounding tissue and/or organs is desired. Such target tissue can be tissue that underwent a surgical procedure, or other procedures such as hysteroscopy, colonoscopy, procedures without incisions, or any combination thereof. Such target tissue can also be tissue adjacent or proximally located to other tissue(s) that underwent a surgical procedure. Non-limiting examples for types of surgical procedures include, among others, abdominal or pelvic operations, surgical incision sites, orthopedic procedures, nasal sinus procedures, neurosurgical procedures, dermatologic procedures, hysteroscopic procedures, vascular procedures, cardiothoracic procedures, reconstructive and cosmetic plastic procedures, and/or ophthalmologic procedures.

The term "disposed onto a/the target tissue" is used to describe a substance, such as a pre-gel ECM mixture, hydrogel, or hydrogel film, that is adhered, placed, applied, disposed, positioned, delivered, attached, immobilized, sprayed, poured, or any combination thereof, onto a target tissue. In some embodiments, a substance, such as a pre-gel ECM mixture, hydrogel, or hydrogel film is disposed onto a surface of the target tissue. In some embodiments, a substance, such as a pre-gel ECM mixture, hydrogel, or hydrogel film is at least partially disposed into the target tissue.

The term "ECM based hydrogel" refers to a gel comprised of components of ECM obtained from a mammalian tissue. In some embodiments, the ECM is from bone. In some embodiments, the bone ECM is from, among others, bovine tissue, porcine tissue, horse tissue, goat tissue, sheep tissue, deer tissue, buffalo tissue, oxen tissue, elk tissue, rabbit tissue, human tissue, or any combination thereof.

The term "maximum dimension" is used to refer to a maximum diameter, thickness, length, width, and/or maximum distance between two opposing points of reference on a pre-gel ECM mixture particle (e.g., droplet, or other types of particles).

The term "average maximum dimension" refers to an average of the maximum dimension for a plurality of particles as described herein (e.g., droplets, or other types of particles).

As used herein, the term "about" in some cases refers to an amount that is approximately the stated amount.

As used herein, the term "about" refers to an amount that is greater or less than the amount by 10%, 5%, or 1%, including increments therein.

As used herein, the term "about" in reference to a percentage refers to an amount that is greater or less the stated percentage by 10%, 5%, or 1%, including increments therein.

As used herein, the term "mixture" refers to a physical combination of two or more substances (e.g., liquids, liquid slurries, partially gelled liquids), wherein in some instances, the physical combination includes a chemical combination or reaction between the two or more substances.

As used herein, the term "pre-gel ECM mixture" or "pre-gel mixture" refers to a combination of an ECM digest and a buffer solution, wherein the ECM digest is a liquid or liquid with solids suspended therein, and the buffer solution is a liquid, and wherein the pre-gel ECM mixture is a liquid under certain conditions but configured to gel when presented with a stimuli. The term "pre-gel ECM mixture" and "pre-gel mixture" are used interchangeably herein.

As used herein, the term "particle" refers to a discrete amount of a substance, such as a droplet of a liquid or a partially gelled liquid, or a droplet of a liquid or partially gelled liquid that has become fully gelled.

As used herein, the term "substantially contemporaneously" refers to the occurrence of two steps or events at or approximately the same time.

As used herein, unless otherwise indicated, the term "collagen to carbohydrate ratio" generally refers to a ratio of the mass (e.g., micrograms) of collagen content in the ECM digest to the mass (e.g., micrograms) of the carbohydrate content in the ECM digest.

The section headings used herein are for organizational purposes only and are not to be construed as limiting the subject matter described.

II. ECM BASED HYDROGEL AND HYDROGEL FILM

Pre-Gel ECM Mixture, Hydrogel, and Hydrogel Film

Disclosed herein, in certain embodiments, are ECM based hydrogels comprising a gelled ECM mixture. In some embodiments, the hydrogels are configured to reduce or inhibit adhesion between a target tissue and adjacent or surrounding tissues by providing an adhesion barrier when disposed onto the target tissue. In some embodiments, the hydrogels comprise a smooth gliding surface that is provided between the target tissue and adjacent or surrounding tissues. In some embodiments, the hydrogel(s) is/are configured as a hydrogel film disposed onto the target tissue.

In some embodiments, the hydrogel film, comprising the gelled ECM mixture, is formed after gelation of a liquid comprising a pre-gel ECM mixture. In some embodiments, the pre-gel ECM mixture comprises an ECM digest that is mixed with a buffer solution. In some embodiments, the ECM digest is neutralized by mixing with the buffer solution. Non-limiting exemplary components and methods for preparing, storing, and retrieving an ECM digest are disclosed herein and further below. In some embodiments, the ECM digest comprises ECM obtained from a mammalian tissue. In some embodiments, the mammalian tissue is bone, intestine, urinary bladder, cardiac tissue, endometrium, dermal tissue, liver tissue, esophageal tissue, brain tissue, spinal cord tissue, or any combination thereof. In some embodiments, the mammalian tissue is bone. In some embodiments, bone tissue is obtained from bovine, porcine, horse, goat, sheep, deer, buffalo, oxen, elk, rabbit, human, or any combination thereof. In some embodiments, the ECM digest comprises a mixture of different types of ECMs. In some embodiments, the ECM comprises hyaluronic acid. In some embodiments, the ECM comprises pepsin. In some embodiments, the ECM digest comprises a collagen to carbohydrate ratio from about 60:1 to about 500:1. As used herein, the collagen to carbohydrate ratio refers to a ratio of the mass (e.g., micrograms) of collagen content in the ECM digest to the mass (e.g., micrograms) of the carbohydrate content in the ECM digest. In some embodiments, the ECM digest comprises a collagen to carbohydrate from about 70:1 to about 400:1. For example, bone ECM is known to comprise a collagen to carbohydrate ratio of at least about 70:1 In some embodiments, the ECM digest comprises a collagen to carbohydrate ratio from about 70:1 to about 120:1. In some embodiments, the ECM digest comprises a collagen to carbohydrate ratio from about 120:1 to about 170:1. In some embodiments, the ECM digest comprises a collagen to carbohydrate ratio from about 170:1 to about 220:1. In some embodiments, the ECM digest comprises a collagen to carbohydrate ratio from about 220:1 to about 270:1. In some embodiments, the ECM digest comprises a collagen to carbohydrate ratio from about 270:1 to about 320:1. In some embodiments, the ECM digest comprises a collagen to carbohydrate ratio from about 320:1 to about 400:1. In some embodiments, the ECM digest comprises a collagen to carbohydrate ratio of at least about 3:1. In some embodiments, the ECM digest comprises a collagen to carbohydrate ratio of at least about 25:1. In some embodiments, the ECM digest comprises a collagen to carbohydrate ratio of at least about 50:1. In some embodiments, the ECM digest comprises a collagen to carbohydrate ratio of at least about 70:1. In some embodiments, the ECM digest comprises a collagen to carbohydrate ratio of at least about 150:1. In some embodiments, the ECM digest comprises a collagen to carbohydrate ratio of at least about 250:1. In some embodiments, the ECM digest comprises a collagen to carbohydrate ratio of at least about 400:1. In some embodiments, the ECM digest comprises a collagen to carbohydrate ratio of at least about 750:1. In some embodiments, the ECM digest comprises a collagen to carbohydrate ratio of at least about 1000:1. In some embodiments, the carbohydrate comprises glycosaminoglycans. In some embodiments, the collagen to carbohydrate ratio refers to a ratio in the ECM and corresponding ECM digest. In some embodiments, the viscosity of an ECM digest will increase as the collagen to carbohydrate ratio increases. In some embodiments, the stiffness of an ECM hydrogel will increase as the collagen to carbohydrate ratio increases.

In some embodiments, the ECM digest is mixed with a buffer solution to neutralize the pH of the ECM digest and/or balance the salt concentration. In some embodiments, the gelation time of the pre-gel ECM mixture can be adjusted by varying the salt concentrations of the pre-gel ECM mixture and/or varying the pH of the buffer solution. In some embodiments, the ECM digest comprises a low pH. For example, in some embodiments, a bone ECM digest has a pH of 2-3. In some embodiments, the buffer solution comprises phosphate-buffered saline (PBS). In some embodiments, the buffer solution comprises PBS and a base. In some embodiments, the buffer solution comprises PBS and NaOH. As referenced herein, an ECM digest neutralized by being mixed with a buffer solution forms a pre-gel ECM mixture. In some embodiments, the pre-gel ECM mixture has a pH of between 7-8. In some embodiments, the pre-gel ECM mixture has a pH between 7.2-7.8.

In some embodiments, the ECM digest and/or the corresponding pre-gel ECM mixture are configured to gel upon exposure to one or more stimuli. As disclosed herein, the characteristics relating to the gelation of the pre-gel ECM mixture and characteristics of the corresponding hydrogels formed from the gelled pre-gel ECM mixture are also applicable to the ECM digest prior to mixing with the buffer solution. In some embodiments, exposure of the pre-gel ECM mixture to one or more stimuli causes the re-polymerization of collagen and/or crosslinking of collagen fibrils within the respective ECM. In some embodiments, stimuli causing gelation of the pre-gel ECM mixture include a prescribed temperature, a prescribed pH range, exposure to a prescribed range of light wavelength, interaction with a chemical, interaction with an enzyme, or any combination thereof. In some embodiments, stimuli causing gelation of the pre-gel ECM mixture include the pre-gel ECM mixture comprising microbubbles carrying stimulatory substances that burst through exposure to ultrasound. In some embodiments, stimuli causing gelation include the pre-gel ECM mixture comprising gold nanoparticles that are targeted with MRI. In some embodiments, stimuli causing gelation include pressure induced gelation, such as through intraabdominal pressure. In some embodiments, stimuli causing gelation using an electric current.

In some embodiments, the pre-gel ECM mixture is thermo-responsive, such that exposure to higher temperatures (e.g., compared to temperature when pre-gel ECM mixture was formed) promotes gelation of the pre-gel ECM mixture. In some embodiments, the pre-gel ECM mixture is configured to gel upon exposure to a temperature between about 25-50° C. In some embodiments, the pre-gel ECM mixture is configured to gel upon exposure to a temperature between about 30-40° C. In some embodiments, the pre-gel ECM mixture is configured to gel upon exposure to a temperature of at least 25° C. In some embodiments, the pre-gel ECM mixture is configured to gel upon exposure to a temperature of at least 30° C. In some embodiments, the pre-gel ECM mixture is configured to gel upon exposure to a temperature of at least 35° C. In some embodiments, the pre-gel ECM mixture is configured to gel upon exposure to at least a normal human body temperature, e.g., about 37° C. In some embodiments, the pre-gel ECM mixture is configured to gel upon exposure to a temperature of at least 40° C.

In some embodiments, the pre-gel ECM mixture is configured to gel upon exposure to a prescribed pH range. In some embodiments, the pre-gel ECM mixture is configured to gel upon exposure to a pH range between 6.5-8.5, such that the pre-gel ECM mixture must be disposed onto the target tissue immediately or soon after being formed, e.g., after mixing the ECM digest with the buffer solution. In some embodiments, the pre-gel ECM mixture is configured to gel upon exposure to a pH range between 7-8. In some embodiments, the pre-gel ECM mixture is configured to gel upon exposure to a pH range between 6.5-7. In some embodiments, the pre-gel ECM mixture is configured to gel upon exposure to a pH range between 6.8-7.3. In some embodiments, the pre-gel ECM mixture is configured to gel upon exposure to a pH range between 7-7.5. In some embodiments, the pre-gel ECM mixture is configured to gel upon exposure to a pH range between 7.5-8. In some embodiments, the pre-gel ECM mixture is configured to gel upon exposure to a pH range between 8-8.5. As described herein, in some embodiments, the gelation time of the pre-gel ECM mixture can be adjusted by varying the pH of the buffer solution. Accordingly, mixing the buffer solution with the ECM digest, as described herein to form a pre-gel ECM mixture, initiates a phase change of said formed pre-gel ECM mixture to form a hydrogel.

In some embodiments, the pre-gel ECM mixture is configured to gel upon exposure to a prescribed salinity range. In some embodiments, the pre-gel ECM mixture is configured to gel upon exposure to a salinity range between 0-0.5 ppt, such that the pre-gel ECM mixture must be disposed onto the target tissue immediately after being neutralized. In some embodiments, the pre-gel ECM mixture is configured to gel upon exposure to a salinity range between 0.5-30 ppt. In some embodiments, the pre-gel ECM mixture is configured to gel upon exposure to a salinity range between of at least 30 ppt. As described herein, in some embodiments, the gelation time of the pre-gel ECM mixture can be adjusted by varying the salt concentrations of the pre-gel ECM mixture.

In some embodiments, the pre-gel ECM mixture is configured to gel upon exposure to light having a prescribed wavelength. In some embodiments, the pre-gel ECM mixture comprises an ECM digest mixed with specific light-reactive polymers, photosensitizers, and/or photo-initiators so as to enable the pre-gel ECM mixture to gel upon exposure to light having a prescribed wavelength. For example, the pre-gel ECM mixture can be configured to gel upon exposure to UV light, infrared light, or any combination thereof. In some embodiments, the light is provided by a light source. In some embodiments, the light source comprises a LED light. In some embodiments, the light comprises a curing light (e.g., as used in dental applications). In some embodiments, the light source comprises a fiber optic laser delivery device.

In some embodiments, the pre-gel ECM mixture is configured to gel upon interacting with a chemical. In some embodiments, the chemical comprises a cross-linker (e.g., glutaraldehyde, Genipin, grape seed extract, epoxy compounds, carbodiimides, other collagen cross linker, or a combination thereof). In some embodiments, the chemical comprises a photocrosslinker (e.g., methacrylate mediated photocrosslinking or riboflavin (RF) and UV exposure). In some embodiments, the chemical comprises an enzyme (e.g., lysyl oxidase).

In some embodiments, the pre-gel ECM mixture is delivered to a target tissue as a plurality of particles ("particles"). In some embodiments, the plurality of particles have an average maximum dimension from about 1 μm to 1000 μm. In some embodiments, the plurality of particles have an average maximum dimension from about 1 μm to 500 μm. As used herein, the maximum dimension corresponds to any dimensional measurement across a particle (or droplet), such as a diameter, thickness, length, width, and/or any two opposing points of reference. In some embodiments, the plurality of particles have an average maximum dimension from about 10 μm to about 500 μm. In some embodiments, the plurality of particles have an average maximum dimension from about 30 μm to about 300 μm. In some embodiments, the plurality of particles have an average maximum dimension from about 30 µm to about 200 µm. In some embodiments, the plurality of particles have an average maximum dimension of at most about 500 µm. In some embodiments, the plurality of particles have an average maximum dimension of at most about 300 µm. In some embodiments, the plurality of particles have an average maximum dimension of about 150 µm. In some embodiments, the plurality of particles have an average maximum dimension of about 100 µm. In some embodiments, the plurality of particles have an average maximum dimension of about 50 µm. In some embodiments, the plurality of particles is a plurality of droplets. In some embodiments, the maximum dimension is a diameter.

Figure 10:
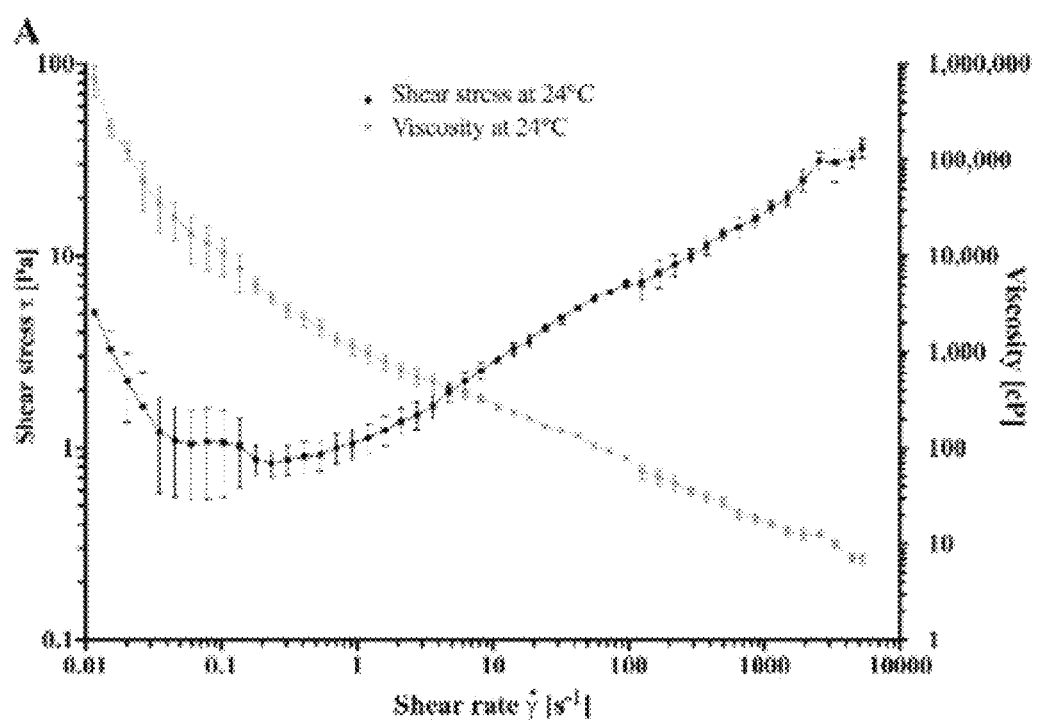
FIG. 10 depicts an exemplary change in viscosity for an exemplary pre-gel ECM mixture based on the shear rate.

In some embodiments, a viscosity of the pre-gel ECM mixture is configured to be reduced when being subject to shear stress. In some embodiments, the viscosity reduces by at least about 10 times when shear rate is applied. For example, in some embodiments, at an applied shear rate of less than 0.1 s$^{-1}$, the viscosity of the pre-gel ECM mixture is at least 1,000 cP, while at an applied shear rate of 1,000 s$^{-1}$, the viscosity of the pre-gel ECM mixture reduces to no more than 100 cP. In some embodiments, the viscosity of the pre-gel ECM mixture reduces from 500,000 Pa to about 100 Pa. FIG. 10 provides an exemplary depiction of the change in viscosity for an exemplary pre-gel ECM mixture (as described herein) based on the amount of shear rate the pre-gel ECM mixture is being subject to.

In some embodiments, as disclosed herein, the pre-gel ECM mixture is disposed onto a target tissue as a plurality of particles. In some embodiments, the target tissue and/or environment surrounding the target tissue ("surrounding environment") provides one or more stimuli that causes gelation of the pre-gel ECM mixture upon being disposed onto said target tissue. For example, in some embodiments, the temperature of the target tissue and/or surrounding environment causes gelation of the pre-gel ECM mixture. In some embodiments, the pre-gel ECM mixture gels upon being disposed onto a target tissue wherein the target tissue and/or surrounding environment having a temperature of at least 35° C. Non-limiting examples of the surrounding environment include other tissues, other organs, interstitial fluid, blood, lymph, G.I. tract, and so on. In some embodiments, the pH of the target tissue and/or surrounding environment further enable gelation of the pre-gel ECM mixture.

In some embodiments, the pre-gel ECM mixture gels between about 1 and 120 seconds after being disposed onto the target tissue. In some embodiments, the pre-gel ECM mixture gels between about 2 and 60 seconds after being disposed onto the target tissue. In some embodiments, the pre-gel ECM mixture gels between about 3 and 30 seconds after being disposed onto the target tissue. In some embodiments, the pre-gel ECM mixture gels between about 4 and 15 seconds after being disposed onto the target tissue. In some embodiments, the pre-gel ECM mixture gels between about 5 and 10 seconds after being disposed onto the target tissue. As described herein, in some embodiments, the gelation time of the pre-gel ECM mixture can be adjusted by varying the salt concentrations of the pre-gel ECM mixture and/or varying the pH of the buffer solution. In some embodiments, the gelation time of the pre-gel ECM mixture can be adjusted by adding one or more dyes to the pre-gel ECM mixture. In some embodiments, the one or more dyes comprise indigo carmine, riboflavin, food/vegetable dyes, and/or methylene blue. In some embodiments, adding the one or more dyes to the pre-gel ECM mixture speeds the gelation time of the pre-gel ECM mixture. In some embodiments, the particles of the one or more dyes act as gelation nucleation sites. In some embodiments, one or more chemically inert particulate additives (e.g., dyes) are mixed with the pre-gel ECM mixture to adjust the gelation speed and/or storage modulus of the hydrogel and/or hydrogel film.

As disclosed herein, in some embodiments, a pre-gel ECM mixture is disposed onto a target tissue as a plurality of pre-gel ECM mixture particles. In some embodiments, each gelled ECM mixture particle forms a hydrogel. In some embodiments, gelation of a plurality of pre-gel ECM mixture particles disposed onto the target tissue forms a hydrogel film disposed onto the target tissue. In some embodiments, the pre-gel ECM mixture conforms to the shape of the target tissue prior to gelation into a hydrogel film. In some embodiments, the pre-gel ECM mixture forms a layer or coating on the target tissue prior to being fully or substantially gelled. In some embodiments, the gelled layer (or coating) of the pre-gel ECM mixture forms the hydrogel film. In some embodiments, the resulting hydrogel film covers at least a portion of the surface of the target tissue. In some embodiments, a plurality of hydrogel films are disposed onto a target tissue. In some embodiments, the plurality of hydrogel films are spaced apart from each other, and cover separate portions of the target tissue surface. In some embodiment, a single hydrogel film or a plurality of hydrogel films cover the entire surface of the target tissue.

In some embodiments, the hydrogel film, as disposed onto the target tissue, has a thickness from about 2 µm to about 10 mm. As referenced herein, in some embodiments, the hydrogel film thickness is measured from a proximal surface of the hydrogel film in contact with the target tissue to a distal surface of the hydrogel film. In some embodiments, the hydrogel film has a thickness from about 100 µm to about 5 mm. In some embodiments, the hydrogel film has a thickness from about 2 µm to about 5 mm, 2 µm to about 3 mm, 2 µm to about 1 mm, 2 µm to about 75 µm. In some embodiments, the hydrogel film has a thickness from about 30 µm to about 5 mm, 30 µm to about 3 mm, 30 µm to about 1 mm, 30 µm to about 75 µm. In some embodiments, the hydrogel film has a thickness from about 1 mm to about 10 mm. In some embodiments, the hydrogel film has a thickness from about 1 mm to about 2 mm, about 1 mm to about 5 mm, about 1 mm to about 10 mm, about 2 mm to about 5 mm, about 2 mm to about 10 mm, or about 5 mm to about 10 mm, including increments therein. In some embodiments, the hydrogel film has a thickness from about 1 mm, about 2 mm, about 5 mm, or about 10 mm. In some embodiments, the hydrogel film has a thickness from at least about 1 mm, about 2 mm, or about 5 mm. In some embodiments, the hydrogel film has a thickness from at most about 2 mm, about 5 mm, or about 10 mm. In some embodiments, the hydrogel film has a thickness of at least 10 µm. In some embodiments, the hydrogel film has a thickness of at least 30 µm. In some embodiments, the hydrogel film has a thickness of at least 100 µm. In some embodiments, the hydrogel film has a thickness of at least 250 µm. In some embodiments, the hydrogel film has a thickness of at least 1 mm. In some embodiments, the hydrogel film has a thickness of at least 2 mm. In some embodiments, the hydrogel film has a thickness of at least 4 mm.

In some embodiments, gelation of each pre-gel ECM mixture particle forms a hydrogel having a storage modulus of at least 250 Pa. In some embodiments, gelation of each pre-gel ECM mixture particle forms a hydrogel having a storage modulus of at least 100 Pa. In some embodiments, gelation of each pre-gel ECM mixture particle forms a hydrogel having a storage modulus of at least 50 Pa. In some embodiments, gelation of the pre-gel ECM mixture forms a hydrogel film having a storage modulus of at least 250 Pa. In some embodiments, the hydrogel film has a storage modulus of at least 500 Pa. In some embodiments, the hydrogel film has a storage modulus of at least 1000 Pa. In some embodiments, the hydrogel has a storage modulus as high as the stiffness of the target tissue. In some embodiments, gelation of the pre-gel ECM mixture forms a hydrogel film having a storage modulus of at least 100 Pa. In some embodiments, gelation of the pre-gel ECM mixture forms a hydrogel film having a storage modulus of at least 75 Pa. In some embodiments, gelation of the pre-gel ECM mixture forms a hydrogel film having a storage modulus of at least 100 Pa. In some embodiments, hydrogel and/or hydrogel film storage modulus can be adjusted based on the type(s) of ECM used in the pre-gel ECM mixture. As described herein, in some embodiments, a chemically inert particulate additive is mixed with the pre-gel ECM mixture to adjust the gelation speed and/or storage modulus of the hydrogel and/or hydrogel film.

In some embodiments, gelation of the pre-gel ECM mixture while being disposed on the target tissue enables the resulting formed hydrogel film to adhere to the target tissue. For example, in some embodiments, gelation of the pre-gel ECM mixture disposed onto the target tissue enables entanglement of the collagen fibrils and/or ECM proteins with 1) the target tissue, 2) adjacent tissue, and/or 3) other collagen fibrils and/or ECM proteins within the hydrogel film (for example from other gelled pre-gel ECM mixture particles). In some embodiments, gelation of pre-gel ECM mixture particles reduced to an average maximum dimension (as referenced herein) of at most about 500 µm enables the resulting formed hydrogel film to adhere faster onto the target tissue and/or remained adhered about the target tissue for an increased duration (as compared to larger particles).

In some embodiments, hydrogel films having a storage modulus of at least 250 Pa and being formed from pre-gel ECM mixture particles having an average maximum dimension at most about 500 µm reduces the total volume of hydrogel film required to treat and/or protect a desired anatomical area, due to the enhanced retention capability. For example, in some embodiments, as disclosed herein, pre-gel ECM mixture particles having an average dimension of at most about 500 µm gel faster and thereby enable for faster tissue adherence by the resulting hydrogel film, while hydrogel film having a storage modulus of at least 100 Pa enable for better retention on the target tissue due to the increased rigidity, strength, durability, and/or abrasion resistance. In some embodiments, the pre-gel ECM mixture is sprayed onto a target tissue thereby aerosolizing the pre-gel ECM mixture into particles having an average maximum dimension of less than about 250 µm, to facilitate faster tissue adherence by the resulting hydrogel film and effective sticking gelling and adhesion prevention. In some embodiments, the pre-gel ECM mixture is sprayed onto a target tissue, thereby aerosolizing the pre-gel ECM mixture into particles having an average maximum dimension of at most about 500 µm, to facilitate faster tissue adherence by the resulting hydrogel film and effective sticking gelling and adhesion prevention. In some embodiments, the spraying of the pre-gel ECM mixture enables a more broad and complete coverage of the surface of the target tissue. In some embodiments, providing the pre-gel ECM as a liquid through a syringe (e.g., a 25 G syringe), enables a specific location of a target tissue to receive the pre-gel ECM. In some embodiments, as described herein, forming the pre-gel ECM mixture (via combining an ECM digest with a buffer solution) occurs substantially contemporaneously with spraying the pre-gel ECM mixture as a plurality of particles, as described herein.

In some embodiments, the hydrogel film is configured to remain adhered onto the target tissue for at least 3 days. In some embodiments, the hydrogel film is configured to remain adhered onto the target tissue for at least 5 days. In some embodiments, the hydrogel film is configured to remain adhered onto the target tissue for at least 6 days. In some embodiments, the hydrogel film is configured to remain adhered onto the target tissue for at least 7 days. In some embodiments, the hydrogel film is configured to remain adhered onto the target tissue for at least 8 days.

In some embodiments, the hydrogel film biodegrades over time (after formation) such that it is substantially or completely degraded after 3 days. In some embodiments, the hydrogel film is substantially or completely degraded after 4 days. In some embodiments, the hydrogel film is substantially or completely degraded after 5 days. In some embodiments, the hydrogel film is substantially or completely degraded after 6 days. In some embodiments, the hydrogel film is substantially or completely degraded after 7 days. In some embodiments, the hydrogel film is substantially or completely degraded after 8 days.

In some embodiments, the hydrogel film provides an adhesion barrier for the target tissue, wherein the hydrogel film comprises a smooth gliding surface that is provided between the target tissue and adjacent or surrounding tissues. For example, in some embodiments, the hydrogel film comprises of collagens, glycosaminoglycans, proteoglycans, and glycoproteins, which have anti-adhesive and water attracting properties.

ECM Based Hydrogel Configured for Tissue Healing

In some embodiments, the hydrogel film is further configured to promote healing of the target tissue and/or tissue surrounding the target tissue. In some embodiments, the ECM of the hydrogel film promotes a favorable, anti-inflammatory immune microenvironment for tissue healing. In some embodiments, such a favorable, anti-inflammatory immune microenvironment is obtained through the effect of the ECM macrophages. For example, in some embodiments, the ECM supports healing through immune modulation by augmenting the macrophage response to injury. The healing response of tissues is dependent upon a heterogeneous population of responding macrophages, which show a phenotypic transition from the pro-inflammatory M1 to the alternatively activated and constructive M2 phenotype. For example, biologic scaffolds derived from mammalian ECM have been used for the repair and reconstruction of a variety of tissues and have been associated with an M2 phenotype. In some embodiments, degradation products from a hydrogel film comprising ECM provides alternatively activated and constructive M2 macrophage polarization, thereby providing an environment for the repair and reconstruction of tissues.

Furthermore, a key process during the initiation of fibrosis/scarring is the epithelial-to-mesenchymal transition (EMT). In some embodiments, the process of EMT is reduced in cells exposed to ECM of a hydrogel film (through degradation of the hydrogel film), thereby reducing the occurrence of fibrosis. In some embodiments, ECM preferentially adheres to inflamed tissue.

In some embodiments, the hydrogel film is configured to act as an excipient to deliver substances that promote healing, tissue regeneration and other therapeutic benefits. In some embodiments, the hydrogel film comprises substances such as small molecules, micro RNA, pharmaceuticals, and/or cells that are covalently bound to and/or physically entrapped within the hydrogel film and configured to reduce inflammation and/or fibrosis, facilitate hemostasis, and/or mitigate leaky bowel anastomosis. In some embodiments, such substances are combined with the ECM digest prior to gelation onto a target tissue. In some embodiments, such substances are delivered upon degradation of the hydrogel film.

Device for ECM Based Hydrogel

In certain embodiments, disclosed herein are devices for reducing postsurgical tissue adhesion using ECM based hydrogels. In some embodiments, the device comprises a pre-gel ECM mixture as disclosed herein, wherein the pre-gel ECM mixture comprises a combination of an ECM digest and buffer solution. In some embodiments, the device comprises an ECM digest and buffer solution, either separately, or combined as a pre-gel ECM mixture. In some embodiments, the device comprises only the ECM digest. As described herein, in some embodiments, the buffer solution is a gel initiator solution, or gel promoter solution, wherein the buffer solution initiates and/or promotes the gelation of the pre-gel ECM mixture when combined with the ECM digest. In some embodiments, the device further comprises a device body, wherein the pre-gel ECM mixture, ECM digest, and/or buffer solution are contained within said device body. In some embodiments, the device is configured to deliver the pre-gel ECM mixture and/or ECM digest. In some embodiments, the device body further comprises an outlet configured to reduce the pre-gel ECM mixture, ECM digest, and/or a buffer solution into a plurality of droplets (or viscous particles) having a prescribed maximum dimension. In some embodiments, the device is configured to aerosolize the pre-gel ECM mixture, ECM digest, and/or a buffer solution into a plurality of droplets (or viscous particles) having a prescribed average maximum dimension. As disclosed herein, the maximum dimension corresponds to any dimensional measurement across a particle, such as a diameter, thickness, length, width, and/or any two opposing points of reference. As disclosed herein, an average maximum dimension refers to an average of the maximum dimension for a plurality of particles. In some embodiments, the device is configured to deliver the particles having an average maximum dimension from about 1 μm to about 500 μm. In some embodiments, the device is configured to deliver the particles having an average maximum dimension from about 10 μm to about 300 μm. In some embodiments, the device is configured to deliver the particles having an average maximum dimension from about 30 μm to about 250 μm. In some embodiments, the device is configured to deliver the particles having an average maximum dimension from about 30 μm to about 100 μm. In some embodiments, the device is configured to deliver the particles having an average maximum dimension of about 250 μm. In some embodiments, the device is configured to deliver the particles having an average maximum dimension of about 100 μm. In some embodiments, the device is configured to deliver the particles having an average maximum dimension of about 50 μm. In some embodiments, the device is configured to deliver the particles having an average maximum dimension of about 30 μm.

In some embodiments, the device body is a syringe. In some embodiments, the syringe is configured to deliver the particles having an average maximum dimension as disclosed herein. In some embodiments, the device body is a spray catheter. In some embodiments the device body is a spray nozzle. In some embodiments, the spray catheter or spray nozzle are configured to spray the particles having an average maximum dimension as disclosed herein. In some embodiments, the device body is a carrier gas. In some embodiments, the device body includes and/or interfaces with a carrier gas. In some embodiments, the device body further comprises an attachment configured to deliver the particles having an average maximum dimension as disclosed herein. In some embodiments the attachment is coupled to the device body. In some embodiments, the attachment is removably coupled to the device body. In some embodiments, the attachment is an atomizer. A non-limiting example of an atomizer is MAD Nasal™ Intranasal Mucosal Atomization Device.

In some embodiments, the device is a multi-device body device ("MDBD") comprising two or more device bodies. In some embodiments, each device body contains a type of fluid to be delivered onto a target tissue. For example, each device body can be configured to contain a pre-gel ECM mixture, an ECM digest, and/or a buffer solution. In some embodiments, each device body contains only one type of fluid. For example, in some embodiments, wherein the device includes two device bodies, a first device body contains an ECM digest, while a second device body contains a buffer solution. In some embodiments, two or more device bodies of a device are configured to simultaneously deliver the respective types of fluid contained therein. In some embodiments, the two or more device bodies share a common outlet for delivering the respective types of fluid. In some embodiments, the common outlet simultaneously delivers two or more types of fluids received from the two or more device bodies. In some embodiments, the common outlet further comprises a mixing tip for mixing the two or more types of fluids from the two or more types of bodies. In some embodiments, each device body of a MDBD is configured to deliver the respective fluid at a prescribed rate. In some embodiments, each MDBD is configured to deliver a desired mixture concentration of two or more fluids. For example, in some embodiments, a first device body of a MDBD is configured to deliver an ECM digest to a common MDBD outlet at a first prescribed rate, while a second device body of a MDBD is configured to deliver a buffer solution to a common MBDB outlet at a second prescribed rate, such that the MDBD is configured to deliver the ECM digest and buffer solution as a neutralized ECM mixture (e.g., pre-gel ECM mixture). In some embodiments, the neutralized ECM mixture has a pH between about 7-8. In some embodiments, as disclosed herein, the MDBD comprises an attachment configured to deliver two or more fluids as particles having an average maximum dimension as disclosed herein. In some embodiments, the MDBD is a dual spray catheter having a mixing tip configured to mix and deliver two or more fluids simultaneously.

In some embodiments, for any device disclosed herein, the device is pressurized so as to deliver the pre-gel ECM mixture, ECM digest, and/or buffer solution at a prescribed rate. In some embodiments, a device is configured to receive pre-gel ECM mixture as a lyophilized powder for delivery onto the target tissue. In some embodiments, the device mixes the lyophilized ECM powder with a buffer solution and delivers a pre-gel ECM mixture onto the target tissue. In some embodiments, the device is configured to deliver pre-gel ECM mixture, among others, using an IV system, through intramuscular delivery, through enema delivery.

In some embodiments, the MDBD may dispose the pre-gel ECM mixture with use of a carrier gas. In some embodiments, the carrier gas may augment delivery of two of more types of fluids. In some embodiments, two or more types of fluids may be mixed before being acted on by the carrier gas. In some embodiments, the carrier gas may have a pressure between 5-15 mmHg. In some embodiments, the carrier gas may have a pressure between 15-25 mmHg. In some embodiments, the carrier gas may have a pressure of at least 25 mmHg. Non-limiting examples of a carrier gas are carbon dioxide, nitrogen, oxygen, helium, etc., or any combination thereof.

In some embodiments, fluid received in a device body is obtained from a respective fluid source. For example, an ECM digest can be obtained from an ECM digest source and inserted into the device body. In another non-limiting example, a buffer solution can be obtained from a source and inserted into the device body. In some embodiments, the device body is coupled to a fluid source so as to receive the fluid directly therefrom. In some embodiments, the device body further comprises a channel or tube coupled to the fluid source. In some embodiments, the device is configured to draw the fluid from the fluid source to the device body. For example, in some embodiments, the device is configured to generate suction to enable the fluid to flow from the source to the device body. In some embodiments, each MBDB device body is coupled to a respective fluid source, so as to enable the respective fluid to directly flow into the respective device body.

Method for Reducing Postsurgical Tissue Adhesion with ECM Based Hydrogel

Disclosed herein, in certain embodiments, are methods for reducing and/or inhibiting tissue adhesion for a target tissue using an ECM based hydrogel. In some embodiments, the method comprises forming particles of a pre-gel mixture comprising an ECM digest and a buffer solution, wherein the ECM digest comprises a collagen to carbohydrate ratio of at least about 70:1, wherein the buffer solution promotes a phase change of the pre-gel mixture to a hydrogel, wherein the particles of the pre-gel mixture have an average maximum dimension of at most 500 μm. In some embodiments, as described herein, forming particles of a pre-gel mixture comprises mixing (combining) the ECM digest and the buffer solution to form the pre-gel mixture, and spraying said formed pre-gel mixture as a plurality of particles (e.g., droplets). In some embodiments, the collagen to carbohydrate ratio is at least about 35:1. In some embodiments, the collagen to carbohydrate ratio is at least about 50:1. In some embodiments, the collagen to carbohydrate ratio is at least about 100:1. In some embodiments, the collagen to carbohydrate ratio is at least about 200:1. In some embodiments, the collagen to carbohydrate ratio is from about 70:1 to about 400:1. In some embodiments, as described herein, the collagen to carbohydrate ratio is based on a mass ratio (i.e., ratio of mass of collagen in ECM digest to mass of carbohydrate in ECM digest). In some embodiments, the mass is in micrograms. In some embodiments, the carbohydrate comprises glycosaminoglycans. In some embodiments, spraying the pre-gel ECM mixture is accomplished through a device described herein (e.g., MDBD). In some embodiments, the mixing of the ECM digest with the buffer solution occurs substantially contemporaneously with the spraying of the pre-gel mixture. In some embodiments, the plurality of particles are in liquid form, partially-gelled liquid form, or fully gelled liquid form when being sprayed. In some embodiments, the pre-gel mixture is delivered as a plurality of particles using other means, such as a syringe, or other type of aerosolization device. In some embodiments, the plurality of particles are in liquid form, partially-gelled liquid form, and/or fully gelled liquid form when being delivered by said other means. In some embodiments, the method further comprises applying the particles of the pre-gel ECM mixture to a target tissue. In some embodiments, the particles of the pre-gel ECM mixture are coated across the entire target tissue. In some embodiments, the method further comprises promoting the formation of a hydrogel by 1) increasing a temperature of the pre-gel mixture to a temperature by presenting the pre-gel mixture to the target tissue at a temperature that is lower than the target tissue (i.e., the temperature of the pre-gel mixture is lower than the temperature of the target tissue), 2) increasing a temperature of the pre-gel mixture by heating the pre-gel mixture 3) exposing the pre-gel mixture to a light source; 4) interacting a chemical with the pre-gel mixture; 5) interacting an enzyme with the pre-gel mixture; or 6) a combination thereof. In some embodiments, the pre-gel mixture is heated using an external heat source. In some embodiments, the pre-gel mixture is heated by the device as it is being sprayed. In some embodiments, the hydrogel forms a hydrogel thin film over the targeted tissue, wherein the hydrogel film is at least about 10 μm thick and comprises a storage modulus of at least 100 Pa. In some embodiments, the hydrogel film is at least about 5 μm thick. In some embodiments, the hydrogel film is at least about 2 μm thick. In some embodiments, the hydrogel film comprises a storage modulus of at least 250 Pa.

In some embodiments, the method comprises disposing a pre-gel ECM mixture, as disclosed herein, onto the target tissue, wherein the target tissue and/or environment surrounding the target tissue ("surrounding environment") causes gelation of the pre-gel ECM mixture to form a hydrogel film having a minimum storage modulus of 100 Pa. As disclosed herein, in some embodiments, the pre-gel ECM mixture comprises a mixture of an ECM digest and a buffer solution. As disclosed herein, in some embodiments, the ECM digest comprises of ECM, obtained from a mammalian tissue, having a collagen to carbohydrate concentration ratio from about 50:1 to about 600:1. In some embodiments, the ECM has a collagen to carbohydrate ratio (by mass, as described herein) from about 70:1 to about 400:1. In some embodiments, the ECM digest comprises one or more types of ECM. In some embodiments, the ECM digest comprises bone ECM. In some embodiments, the pre-gel ECM mixture is disposed onto the target tissue as a plurality of droplets (or viscous particles). In some embodiments, the method comprises spraying the pre-gel ECM mixture as a plurality of droplets (or viscous particles) onto the target tissue. In some embodiments, spraying the pre-gel ECM mixture comprises aerosolizing the pre-gel ECM mixture as a plurality of droplets. In some embodiments, the particles each have an average maximum dimension as disclosed herein, such as from about 1 μm to about 1000 μm, about 10 μm to about 500 μm, about 30 μm to about 250 μm, about 30 μm to about 100 μm, at most 30 μm, at most about 100 μm, at most about 250 μm, at most about 500 μm or any combination thereof. As disclosed herein, the maximum dimension corresponds to any dimensional measurement across a particle, such as a diameter, thickness, length, width, and/or any two opposing points of reference.

In some embodiments, disposing the pre-gel ECM mixture onto the target tissue further comprises using a device, as disclosed herein, wherein the device is configured to reduce and deliver the pre-gel ECM mixture as a plurality of particles having an average maximum dimension as disclosed herein. In some embodiments, the device is a syringe, a spray nozzle, or a spray catheter. In some embodiments, the catheter or similar component is steerable. In some embodiments, the device includes an attachment configured to reduce and deliver the particles onto the target tissue with an average maximum dimension as disclosed herein. In some embodiments, the attachment is an atomizer.

In some embodiments, the method comprises mixing (combining) the ECM digest and buffer solution, to form a pre-gel ECM mixture, and subsequently inserting the pre-gel ECM mixture into a device for delivery onto a target tissue. In some embodiments, the ECM digest, when in liquid form, is mixed with a buffer solution and disposed onto the target tissue using a MDBD, as disclosed herein. In some embodiments, the MDBD is a dual spray catheter. In some embodiments, the dual spray catheter comprises a mixing tip. In some embodiments, the pre-gel ECM mixture is sprayed onto the target tissue. In some embodiments, the method comprises spraying pre-gel ECM mixture uniformly onto and about the target tissue. In some embodiments, the pre-gel ECM mixture is sprayed onto the target tissue until a coating of the pre-gel ECM mixture is formed over the target tissue. In some embodiments, the pre-gel ECM mixture is sprayed onto separate portions of a target tissue.

In some embodiments, the method further comprises preparing the pre-gel ECM mixture to be disposed onto the target tissue. As disclosed herein, in some embodiments, the pre-gel ECM mixture comprises of an ECM digest as disclosed herein mixed with a buffer solution. In some embodiments, the buffer solution comprises NaOH and Phosphate-buffered saline (PBS). In some embodiments, the ECM digest is obtained via the preparation method disclosed herein further below. In some embodiments, the prepared ECM digest is mixed with the buffer solution immediately prior to being disposed onto the target tissue. In some embodiments, the ECM digest is obtained from a previously prepared ECM digest that was configured for storage. In some embodiments, the previously prepared ECM digest is stored as a dry lyophilized powder. In some embodiments, ECM digest as a dry lyophilized powder is reconstituted immediately prior to being disposed onto the target tissue. In some embodiments, the dry lyophilized powder is reconstituted using a buffer solution, as disclosed herein, so as to form a pre-gel ECM mixture. In some embodiments, the pre-gel ECM mixture obtained from dry lyophilized powder is delivered onto the target tissue using a device as disclosed herein. In some embodiments, previously prepared ECM digest is stored as viscous liquid pre-gel solution and/or a frozen pre-gel solution at a temperature below 4° C. In some embodiments, the viscous liquid pre-gel solution is at a temperature between −20 and 4° C. In some embodiments, the frozen pre-gel solution is at a temperature between −80 and −20° C. In some embodiments, the viscous liquid pre-gel solution is mixed with the buffer solution immediately prior to being disposed onto the target tissue, so as to form a pre-gel ECM mixture. In some embodiments, the viscous liquid pre-gel solution is mixed with a buffer solution and immediately inserted into a device for delivery onto a target tissue. In some embodiments, the viscous liquid pre-gel solution and buffer solution are disposed onto a target tissue using a MDBD as disclosed herein, e.g., dual spray catheter. In some embodiments, the pre-gel ECM mixture is also mixed with one or more chemically inert particulate additives. In some embodiments, the pre-gel ECM mixture is also mixed with one or more dyes. In some embodiments, the one or more dyes comprise indigo carmine and/or methylene blue. In some embodiments, the one or more chemically inert particulate additives and/or one or more dyes are mixed with buffer solution and ECM digest simultaneously or sequentially.

In some embodiments, as disclosed herein, the target tissue and/or environment surrounding the target tissue (surrounding environment) provides one or more stimuli that causes gelation of the pre-gel ECM mixture when disposed onto said target tissue. In some embodiments, as disclosed herein, the pre-gel ECM mixture gels when exposed to a target tissue temperature and/or surrounding environment of at least 25-50° C. In some embodiments, the pre-gel ECM mixture gels when exposed to a target tissue temperature and/or surrounding environment of at least 35° C.

In some embodiments, as disclosed herein, the pre-gel ECM mixture further comprises a photo-initiator, photosensitizer, and/or light-reactive polymer, so as to gel upon being exposed to a given light wavelength. In some embodiments, the method further comprises providing and/or shining a light onto the target tissue having the pre-gel ECM mixture disposed thereon, thereby causing gelation of said pre-gel ECM mixture. In some embodiments, the light is UV light and/or infrared light.

In some embodiments, the pre-gel ECM mixture is delivered from a prescribed distance away from the target tissue. In some embodiments, the pre-gel ECM mixture is delivered to the target tissue after waiting a prescribed time after completion of the surgical procedure.

As disclosed herein, in some embodiments, gelation of the pre-gel ECM mixture disposed onto the target tissue forms a hydrogel film. In some embodiments, as disclosed herein, the pre-gel ECM mixture is disposed onto the target tissue as a plurality of particles. In some embodiments, the pre-gel ECM mixture is disposed onto separate portions of a target tissue, thereby forming a plurality of hydrogel films. In some embodiments, each resulting formed hydrogel film has a storage modulus of at least 250 Pa. In some embodiments, each resulting formed hydrogel film have a storage modulus of at least 250 Pa, 500 Pa, 1000 Pa, or any combination thereof.

As disclosed herein, in some embodiments, a hydrogel film disposed on the target tissue has a thickness from about 10 μm to 10 mm. In some embodiments, as disclosed herein, the hydrogel film has a thickness from about 1 mm to 2 mm. In some embodiments, the hydrogel film covers at least portion of the surface of the target tissue.

In some embodiments, the hydrogel film is configured to adhere to the target tissue upon gelation. In some embodiments, as disclosed herein, the hydrogel film is configured to remain adhered onto the target tissue for at least 3, 4, 5, 6, 7, and/or 8 days. In some embodiments, as disclosed herein, the hydrogel film biodegrades over time (after formation) such that it is substantially or completely degraded after 3, 4, 5, 6, 7, and/or 8 days.

III. ECM BASED HYDROGELS MODIFIED WITH A CROSS-LINKING AGENT

In some embodiments, the ECM based hydrogel and/or hydrogel film, as disclosed herein, further comprises a crosslinking agent. In some embodiments, the modified hydrogel films are formed through gelation of a pre-gel ECM mixture, as disclosed herein, mixed with a crosslinking agent. In some embodiments, crosslinking the pre-gel ECM mixture provides for more rapid gelation, increased stiffness, and/or enables for better adherence of the hydrogel film to a target tissue. In some embodiments, crosslinked hydrogel films comprise ECM having a collagen to carbohydrate concentration ratio of at least 70:1. In some embodiments, hydrogel films formed through crosslinking and comprising ECM with a collagen to carbohydrate ratio (by mass) of at least 70:1 have a storage modulus of at least 50

Pa, 100 Pa, 250 Pa, 500 Pa, 1000 Pa, at least a storage modulus as high as the stiffness of the target tissue, or any combination thereof.

In some embodiments, a crosslinking agent is mixed with a pre-gel ECM mixture and/or ECM digest, as disclosed herein, prior to disposing the pre-gel ECM mixture onto a target tissue. In some embodiments, the crosslinking agent is disposed onto the target tissue simultaneously with a pre-gel ECM mixture. In some embodiments, the crosslinking agent is disposed onto the target tissue simultaneously with an ECM digest and buffer solution. In some embodiments, the crosslinking agent is dispersed with the pre-gel ECM mixture, thereby providing a distributed mixture of the pre-gel ECM mixture and crosslinking agent. In some embodiments, the crosslinking agent is dispersed with the ECM digest and buffer solution, thereby providing a distributed mixture of the ECM digest, buffer solution and crosslinking agent.

In some embodiments, the crosslinking agent is glutaraldehyde, genipin, carbodiimides, acrylates, oligourethanes, polyphenols from natural resources (e.g., cashew nut shell liquid and from Aroeira extract, among others), or any combination thereof.

In some embodiments, crosslinking the ECM material changes the hydrophobicity of the material and provides increased resistance to hydrogel degradation.

In some embodiments, the crosslinked hydrogel films have the same thickness as the hydrogel films disclosed herein for the non-crosslinked hydrogel film, such as from about 10 µm to about 10 mm and/or about 1 mm to about 2 mm. In some embodiments, the crosslinked hydrogel films are configured to adhere to the target tissue for the same duration as disclosed herein for the non-crosslinked hydrogel film, such as for 3, 4, 5, 6, 7, or 8 days. In some embodiments, the cross-linked hydrogel films are configured to degrade over time (after formation), so as to substantially degrade over the same duration as for non-crosslinked hydrogel film disclosed herein, such as over 3, 4, 5, 6, 7, or 8 days.

Device for Reducing Adhesion with ECM Based Hydrogel and Crosslinking Agent

Disclosed herein, in some embodiments, is a device for simultaneously delivering pre-ECM gel mixture, as disclosed herein, with a crosslinking agent onto a target tissue. In some embodiments, the device is the same as an MDBD disclosed herein, further comprising a crosslinking agent. In some embodiments, the MDBD comprises two device bodies, wherein the pre-ECM gel mixture is contained in one device body, and the crosslinking agent is contained in another device body. In some embodiments, the MDBD comprises three device bodies, wherein an ECM digest, buffer solution, and crosslinking agent are all contained in a respective device body.

In some embodiments, the crosslinking agent is delivered to the target tissue with the pre-gel ECM mixture through a common outlet. In some embodiments, the common outlet comprises a mixing tip. In some embodiments, the crosslinking agent is delivered to the target tissue with the pre-gel ECM mixture through separate outlets.

As disclosed herein, in some embodiments, the MDBD for crosslinking a pre-gel ECM mixture is configured to deliver a pre-gel ECM mixture and crosslinking agent onto the target tissue having an average maximum dimension as disclosed herein. For example, in some embodiments, the mixture of the pre-gel ECM mixture and crosslinking agent is configured to be delivered to the target tissue as a plurality of particles having an average maximum dimension, such as diameter, of from about 1 µm to about 1000 µm, 10 µm to about 500 µm, 30 µm to about 250 µm, 30 µm to about 100 µm, at most 30 µm, at most about 100 µm, at most about 250 µm, and/or at most about 500 µm. In some embodiments, the mixture of the pre-gel ECM mixture and crosslinking agent is configured to be aerosolized and delivered to the target tissue as a plurality of droplets (or viscous particles) having a prescribed maximum dimension as described herein.

Method for Reducing Adhesion with ECM Based Hydrogel and Cross-Linking Agent

Disclosed herein, in some embodiments, are methods for reducing and/or inhibiting tissue adhesion for a target tissue using a crosslinked hydrogel film. In some embodiments, the method comprises the method disclosed herein for non-crosslinked ECM based hydrogels, and further comprises delivering a crosslinking agent to the target tissue with the pre-gel ECM mixture. In some embodiments, the crosslinking agent is delivered simultaneously with the pre-gel ECM mixture.

IV. HYDROGEL COMPRISING SYNTHETIC AND NATURALLY DERIVED MATERIALS

Synthetic Pre-Gel, Synthetic Hydrogel and Synthetic Hydrogel Film

Disclosed herein, in certain embodiments, are synthetic hydrogels comprising a gelled synthetic mixture. In some embodiments, the synthetic hydrogels are configured to reduce or inhibit adhesion between a target tissue and adjacent or surrounding tissues by providing an adhesion barrier when disposed onto the target tissue. In some embodiments, the synthetic hydrogels comprise a smooth gliding surface that is provided between the target tissue and adjacent or surrounding tissues. In some embodiments, the synthetic hydrogels are configured as a synthetic hydrogel film disposed onto the target tissue.

In some embodiments, the synthetic hydrogel film, comprising the gelled synthetic mixture, is formed after gelation of a liquid comprising a pre-gel synthetic mixture. In some embodiments, the pre-gel synthetic mixture comprises only of synthetic material. In some embodiments, the pre-gel synthetic mixture comprises of synthetic and naturally-derived materials. In some embodiments, the synthetic mixture comprises Pluronic F127 (a triblock copolymer consisting of a central hydrophobic block of polypropylene glycol flanked by two hydrophilic blocks of polyethylene glycol). In some embodiments, the synthetic mixture comprises polyethylene glycol (PEG), polyethylene oxide (PEO), polyvinyl alcohol (PVA), hyaluronic acid (HA), carboxymethyl cellulose (CMC), polycaprolactone (PCL), platelet rich plasma (PRP), sealants, hemostasis agents, mesenchymal stem cells (MSCs), glues (e.g., dermabond component), or any combination thereof.

In some embodiments, the pre-gel synthetic mixtures are configured to gel upon exposure to one or more stimuli. In some embodiments, stimuli causing gelation of the pre-gel synthetic mixture include a prescribed temperature, a prescribed pH range, a prescribed range of light wavelength, a prescribed concentration of $CO_2$, or any combination thereof.

In some embodiments, the pre-gel synthetic mixture is thermo-responsive, such that the pre-gel synthetic mixture is configured to gel upon exposure to a prescribed temperature. In some embodiments, the pre-gel synthetic mixture is configured to gel upon exposure to a temperature between about 25-50° C. In some embodiments, the pre-gel synthetic mixture is configured to gel upon exposure to a temperature between about 30-40° C. In some embodiments, the pre-gel synthetic mixture is configured to gel upon exposure to a temperature of at least 25° C. In some embodiments, the pre-gel synthetic mixture is configured to gel upon exposure to a temperature of at least 30° C. In some embodiments, the pre-gel synthetic mixture is configured to gel upon exposure to a temperature of at least 35° C. In some embodiments, the pre-gel synthetic mixture is configured to gel upon exposure to at least a normal human body temperature, e.g., about 37° C. In some embodiments, the pre-gel synthetic mixture is configured to gel upon exposure to a temperature of at least 40° C.

In some embodiments, the pre-gel synthetic mixture is configured to gel upon exposure to a prescribed salinity range. In some embodiments, the pre-gel synthetic mixture is configured to gel upon exposure to a salinity range between 0-0.5 ppt, such that the pre-gel synthetic mixture must be disposed onto the target tissue immediately after being formed. In some embodiments, the pre-gel synthetic mixture is configured to gel upon exposure to a salinity range between 0.5-30 ppt. In some embodiments, the pre-gel synthetic mixture is configured to gel upon exposure to a salinity range between of at least 30 ppt.

In some embodiments, the pre-gel synthetic mixture is configured to gel upon exposure to light having a prescribed wavelength. In some embodiments, the pre-gel synthetic mixture is mixed with specific light-reactive polymers, photosensitizers, and/or photo-initiators so as to enable the pre-gel synthetic mixture to gel upon exposure to light having a desired wavelength. For example, the pre-gel synthetic mixture can be configured to gel upon exposure to UV light, infrared light, or any combination thereof.

In some embodiments, the pre-gel synthetic mixture comprises a plurality of viscous particles ("synthetic particles") of the synthetic mixture. In some embodiments, the plurality of synthetic particles each have an average maximum dimension between from about 1 µm to about 1000 µm. In some embodiments, the plurality of synthetic particles each have an average maximum dimension between from about 1 µm to about 500 µm. As used herein, the maximum dimension corresponds to any dimensional measurement across a synthetic particle, such as a diameter, thickness, length, width, and/or any two opposing points of reference. In some embodiments, the plurality of synthetic particles each have an average maximum dimension from about 10 µm to about 500 µm. In some embodiments, the plurality of synthetic particles have an average maximum dimension from about 30 µm to about 500 µm. In some embodiments, the plurality of synthetic particles have an average maximum dimension from about 30 µm to about 250 µm. In some embodiments, the plurality of synthetic particles have an average maximum dimension from about 30 µm to about 100 µm. In some embodiments, the plurality of synthetic particles have an average maximum dimension of about 250 µm. In some embodiments, the plurality of synthetic particles have an average maximum dimension of about 100 µm. In some embodiments, the plurality of synthetic particles have an average maximum dimension of about 50 µm. In some embodiments, the plurality of synthetic particles have an average maximum dimension of about 30 µm. In some embodiments, the plurality of synthetic particles have an average maximum dimension of about 10 µm.

In some embodiments, as disclosed herein, the pre-gel synthetic mixture is disposed onto a target tissue as a plurality of synthetic particles. In some embodiments, the target tissue and/or environment surrounding the target tissue ("surrounding environment") provides one or more stimuli that causes gelation of the pre-gel synthetic mixture upon being disposed onto the target tissue. For example, in some embodiments, the temperature of the target tissue and/or surrounding environment causes gelation of the pre-gel synthetic mixture. In some embodiments, the pre-gel synthetic mixture gels upon being disposed onto a target tissue wherein the target tissue and/or surrounding environment have a temperature of at least about room temperature, at least about 25° C., at least about 30° C., at least about 35° C., or at least about human body temperature. Non-limiting examples of the surrounding environment include other tissues, other organs, interstitial fluid, blood, lymph, GI tract, and so on. In some embodiments, the pH of the target tissue and/or surrounding environment further enable gelation of the pre-gel synthetic mixture.

In some embodiments, the pre-gel synthetic mixture gels between 1 and 120 seconds after being disposed onto the target tissue. In some embodiments, the pre-gel synthetic mixture gels between 2 and 60 seconds after being disposed onto the target tissue. In some embodiments, the pre-gel synthetic mixture gels between 3 and 30 seconds after being disposed onto the target tissue. In some embodiments, the pre-gel synthetic mixture gels between 4 and 15 seconds after being disposed onto the target tissue. In some embodiments, the pre-gel synthetic mixture gels between 5 and 10 seconds after being disposed onto the target tissue.

As disclosed herein, in some embodiments, a pre-gel synthetic mixture is disposed onto a target tissue as a plurality of pre-gel synthetic mixture synthetic particles. In some embodiments, each gelled synthetic mixture particle forms a synthetic hydrogel. In some embodiments, the gelation of a plurality of pre-gel synthetic mixture synthetic particles forms a synthetic hydrogel film disposed onto the target tissue. In some embodiments, the pre-gel synthetic mixture conforms to the shape of the target tissue prior to gelation into a synthetic hydrogel film. In some embodiments, the resulting synthetic hydrogel film covers at least a portion of the surface of the target tissue. In some embodiments, a plurality of synthetic hydrogel films are disposed onto a target tissue. In some embodiments, the plurality of synthetic hydrogel films are spaced apart from each other, and cover separate portions of the target tissue surface.

In some embodiments, the synthetic hydrogel film, as disposed onto the target tissue, has a thickness from about 10 µm to about 10 mm. As referenced herein, in some embodiments, the synthetic hydrogel film thickness is measured from a proximal surface of the hydrogel film in contact with the target tissue to a distal surface of the hydrogel film. In some embodiments, the synthetic hydrogel film has a thickness from about 100 µm to about 5 mm. In some embodiments, the synthetic hydrogel film has a thickness from about 1 mm to about 2 mm. In some embodiments, the synthetic hydrogel film has a thickness of at least 30 µm. In some embodiments, the synthetic hydrogel film has a thickness of at least 100 µm. In some embodiments, the synthetic hydrogel film has a thickness of at least 250 µm. In some embodiments, the synthetic hydrogel film has a thickness of at least 1 mm. In some embodiments, the synthetic hydrogel film has a thickness of at least 2 mm. In some embodiments, the synthetic hydrogel film has a thickness of at least 4 mm.

In some embodiments, gelation of each pre-gel synthetic mixture particle forms a synthetic hydrogel having a storage modulus of at least 100 Pa. In some embodiments, gelation of the pre-gel synthetic mixture forms a synthetic hydrogel film having a storage modulus of at least 50 Pa. In some embodiments, gelation of the pre-gel synthetic mixture forms a synthetic hydrogel film having a storage modulus of at least 100 Pa. In some embodiments, gelation of the pre-gel synthetic mixture forms a synthetic hydrogel film having a storage modulus of at least 250 Pa. In some embodiments, the synthetic hydrogel film has a storage modules of at least 500 Pa. In some embodiments, the synthetic hydrogel film has a storage modules of at least 1000 Pa. In some embodiments, the synthetic hydrogel film has a storage modulus as high as the stiffness of the target tissue.

In some embodiments, gelation of the pre-gel synthetic mixture while being disposed on the target tissue enables the resulting formed synthetic hydrogel film to adhere to the target tissue.

In some embodiments, synthetic hydrogel film having a storage modulus of at least 100 Pa and being formed from pre-gel synthetic mixture particles having an average maximum dimension less than about 500 μm reduces the total volume of synthetic hydrogel film required to treat a desired anatomical area, due to the enhanced retention capability.

In some embodiments, the synthetic hydrogel film is configured to remain adhered onto the target tissue for at least 3 days. In some embodiments, the synthetic hydrogel film is configured to remain adhered onto the target tissue for at least 5 days. In some embodiments, the synthetic hydrogel film is configured to remain adhered onto the target tissue for at least 6 days. In some embodiments, the synthetic hydrogel film is configured to remain adhered onto the target tissue for at least 7 days. In some embodiments, the synthetic hydrogel film is configured to remain adhered onto the target tissue for at least 8 days.

In some embodiments, the synthetic hydrogel and/or synthetic hydrogel film biodegrades over time (after formation) such that it is substantially or completely degraded after 3 days. In some embodiments, the synthetic hydrogel and/or synthetic hydrogel film is substantially or completely degraded after 4 days. In some embodiments, the synthetic hydrogel and/or synthetic hydrogel film is substantially or completely degraded after 5 days. In some embodiments, the synthetic hydrogel and/or synthetic film is substantially or completely degraded after 6 days. In some embodiments, the synthetic hydrogel and/or synthetic hydrogel film is substantially or completely degraded after 7 days. In some embodiments, the synthetic hydrogel and/or synthetic hydrogel film is substantially or completely degraded after 8 days.

In some embodiments, the synthetic hydrogel film provides an adhesion barrier for the target tissue.

Device for Synthetic Hydrogel

In certain embodiments, disclosed herein is a device for reducing postsurgical tissue adhesion. In some embodiments, the device comprises a pre-gel synthetic mixture, wherein the pre-gel synthetic mixture is as disclosed herein, and the device further comprises a device body for containing the pre-gel synthetic mixture. In some embodiments, the device body further comprises an outlet configured to reduce the pre-gel synthetic mixture into a plurality of synthetic droplets (or viscous particles) having a prescribed maximum dimension. In some embodiments, the device is configured to aerosolize the pre-gel synthetic mixture into a plurality of droplets (or viscous particles) having a prescribed maximum dimension. As disclosed herein, the maximum dimension corresponds to any dimensional measurement across a synthetic particle, such as a diameter, thickness, length, width, and/or any two opposing points of reference. In some embodiments, the device is configured to deliver the synthetic particles having an average maximum dimension from about 1 μm to about 1000 μm. In some embodiments, the device is configured to deliver the synthetic particles having an average maximum dimension from about 1 μm to about 500 μm. In some embodiments, the device is configured to deliver the synthetic particles having an average maximum dimension from about 10 μm to about 300 μm. In some embodiments, the device is configured to deliver the synthetic particles having an average maximum dimension from about 30 μm to about 250 μm. In some embodiments, the device is configured to deliver the synthetic particles having an average maximum dimension from about 30 μm to about 100 μm. In some embodiments, the device is configured to deliver the synthetic particles having an average maximum dimension of about 500 μm. In some embodiments, the device is configured to deliver the synthetic particles having an average maximum dimension of about 250 μm. In some embodiments, the device is configured to deliver the synthetic particles having an average maximum dimension of about 100 μm. In some embodiments, the device is configured to deliver the synthetic particles having an average maximum dimension of about 50 μm. In some embodiments, the device is configured to deliver the synthetic particles having an average maximum dimension of about 30 μm.

In some embodiments, the device body is a syringe. In some embodiments, the syringe is configured to deliver the synthetic particles with a maximum diameter. In some embodiments, the device body is a spray catheter. In some embodiments the device body is a spray nozzle. In some embodiments, the catheter or similar component is steerable. In some embodiments, the spray catheter or spray nozzle are configured to spray the synthetic particles with a prescribed maximum diameter, as disclosed herein. In some embodiments, the device body is a carrier gas. In some embodiments, the device body includes and/or interfaces with a carrier gas. In some embodiments, the device body further comprises an attachment configured to deliver the synthetic particles each with an average maximum dimension having any combination of the ranges and limitations as disclosed herein. In some embodiments the attachment is coupled to the device body. In some embodiments, the attachment is removably coupled to the device body. In some embodiments, the attachment is an atomizer. A non-limiting example of an atomizer is MAD Nasal™ Intranasal Mucosal Atomization Device.

In some embodiments, fluid received in a device body is obtained from a source. For example, a pre-gel synthetic mixture can be obtained from a source and inserted into the device body. In some embodiments, the device body is coupled to a fluid source so as to receive the fluid directly therefrom. In some embodiments, the device body further comprises a channel or tube coupled to the fluid source. In some embodiments, the device is configured to draw the fluid from the fluid source to the device body. For example, in some embodiments, the device is configured to generate suction to enable the fluid to flow from the source to the device body.

Method for Reducing Postsurgical Tissue Adhesion with Synthetic Hydrogel Film

Disclosed herein, in some embodiments, are methods for reducing and/or inhibiting tissue adhesion for a target tissue using synthetic hydrogel film. In some embodiments, the method comprises disposing a pre-gel synthetic mixture, as disclosed herein, onto the target tissue, wherein the target tissue and/or environment surrounding the target tissue ("surrounding environment") causes gelation of the pre-gel synthetic mixture to form a synthetic hydrogel film having a minimum storage modulus of 250 Pa. As disclosed herein, in some embodiments, the pre-gel synthetic mixture comprises a mixture of synthetic and naturally-derived materials.

As disclosed herein, in some embodiments, the synthetic mixture comprises Pluronic F127. In some embodiments, the pre-gel synthetic mixture is disposed onto the target tissue as a plurality of synthetic particles (or viscous particles). In some embodiments, the synthetic particles each have an average maximum dimension having ranges and limitations as disclosed herein, such as about 1 µm to about 500 µm, about 10 µm to about 300 µm, about 30 µm to about 250 µm, about 30 µm to about 100 µm, at most 30 µm, at most 100 µm, at most 250 µm, or any combination thereof. As disclosed herein, the maximum dimension corresponds to any dimensional measurement across a particle, such as a diameter, thickness, length, width, and/or any two opposing points of reference.

In some embodiments, disposing the pre-gel synthetic mixture onto the target tissue further comprises using a device, as disclosed herein, configured to reduce and deliver the pre-gel synthetic mixture as a plurality of synthetic particles having an average maximum dimension as disclosed herein. In some embodiments, the device is a syringe, a spray nozzle, or a spray catheter. In some embodiments, disposing the pre-gel synthetic mixture onto the target tissue comprises aerosolizing the pre-gel synthetic mixture. In some embodiments, the device includes an attachment configured to reduce and deliver the particles onto the target tissue with an average maximum dimension as disclosed herein. In some embodiments, the attachment is an atomizer. In some embodiments, the pre-gel synthetic mixture is sprayed onto the target tissue. In some embodiments, the pre-gel synthetic mixture is sprayed uniformly onto and about the target tissue. In some embodiments, the pre-gel synthetic mixture is sprayed onto the target tissue until a coating of the pre-gel synthetic mixture is formed over the target tissue. In some embodiments, the pre-gel synthetic mixture is sprayed onto separate portions of a target tissue.

In some embodiments, the method further comprises preparing the pre-gel synthetic mixture to be disposed onto the target tissue. As disclosed herein, in some embodiments, the pre-gel synthetic mixture comprises of a mixture of synthetic and naturally-derived materials.

In some embodiments, as disclosed herein, the target tissue and/or environment surrounding the target tissue (surrounding environment) provides one or more stimuli that causes gelation of the pre-gel synthetic mixture when disposed onto said target tissue. In some embodiments, as disclosed herein, the pre-gel synthetic mixture gels when exposed to a target tissue temperature and/or surrounding environment of at least 25-50° C. In some embodiments, the pre-gel synthetic mixture gels when exposed to a target tissue temperature and/or surrounding environment of at least 35° C.

In some embodiments, as disclosed herein, the pre-gel synthetic mixture further comprises a photo-initiator, photosensitizer, and/or light-reactive polymer, so as to cause gelation upon exposure to a given light wavelength. In some embodiments, the method further comprises providing and/or shining a light onto the target tissue having the pre-gel synthetic mixture disposed thereon, thereby causing gelation of said pre-gel synthetic mixture. In some embodiments, the light is UV light and/or infrared light.

In some embodiments, the pre-gel synthetic mixture is delivered from a prescribed distance away from the target tissue. In some embodiments, the pre-gel synthetic mixture is delivered to the target tissue after waiting a prescribed time after completion of the surgical procedure.

As disclosed herein, in some embodiments, gelation of the pre-gel synthetic mixture disposed onto the target tissue forms a synthetic hydrogel film. In some embodiments, as disclosed herein, the pre-gel synthetic mixture is disposed onto the target tissue as a plurality of synthetic particles. In some embodiments, the pre-gel synthetic mixture is disposed onto separate portions of a target tissue, thereby forming a plurality of synthetic hydrogel films. In some embodiments, each resulting synthetic hydrogel film has a storage modulus of at least 250 Pa. In some embodiments, each resulting synthetic hydrogel film has a storage modulus of at least 250 Pa, 500 Pa, 1000 Pa, or any combination thereof.

As disclosed herein, in some embodiments, the synthetic hydrogel film disposed on the target tissue has a thickness of about 10 µm to about 10 mm. In some embodiments, as disclosed herein, the synthetic hydrogel film has a thickness of about 1 mm to about 2 mm. In some embodiments, the synthetic hydrogel film covers at least portion of the surface of the target tissue.

In some embodiments, the synthetic hydrogel film is configured to adhere to the target tissue upon gelation. In some embodiments, as disclosed herein, the synthetic hydrogel film is configured to remain adhered onto the target tissue for at least 3, 4, 5, 6, 7, and/or 8 days. In some embodiments, the synthetic hydrogel film biodegrades over time (after formation), as disclosed herein, such that it is substantially or completely degraded after 3, 4, 5, 6, 7, and/or 8 days.

V. ADDITIONAL THERAPEUTIC BENEFITS FOR USE OF HYDROGELS DISCLOSED HEREIN

In certain embodiments, the hydrogel/hydrogel film disclosed herein provides additional therapeutic benefits, in addition to reducing and/or inhibiting tissue adhesion. In certain embodiments, a hydrogel/hydrogel film, as disclosed herein, is used to reduce and/or inhibit infection a bacterial contaminated field after a surgical procedure. In certain embodiments, a hydrogel/hydrogel film, as disclosed herein, is used for reducing and/or inhibiting cancer growth and/or recurrence in cancerous tissue or areas with a known history of cancer. In certain embodiments, a hydrogel/hydrogel film, as disclosed herein, is used for reducing and/or inhibiting leakage or adhesions on an anastomic site. In certain embodiments, a hydrogel/hydrogel film, as disclosed herein, is used for reducing and/or inhibiting scarring and/or keloid formation on an incisional site. In certain embodiments, a hydrogel/hydrogel film, as disclosed herein, is used as an instillate for reducing and/or inhibiting tissue adherence, and/or lubricating organs after a surgical procedure. In certain embodiments, a hydrogel/hydrogel film, as disclosed herein, is used for coating the surface of synthetic implants to reduce and/or inhibit scarring/foreign body response, such as meshes for hernia, pelvic organ repair, pacemakers, breast implants, and so on. In certain embodiments, a hydrogel/hydrogel film, as disclosed herein, is used for reducing and/or inhibiting occlusion of a peritoneal dialysis catheter. In certain embodiments, a hydrogel/hydrogel film, as disclosed herein, is used for coating thoracic and/or abdominal drain lines. In certain embodiments, a hydrogel/hydrogel film, as disclosed herein, is used for joint arthroscopic operation to reduce and/or inhibit adhesions. In certain embodiments, a hydrogel/hydrogel film, as disclosed herein, is used for reducing and/or inhibiting scarring in dupuytren's and trigger finger procedures, tendinous, and ligamentous repair procedures. In certain embodiments, a hydrogel/hydrogel film, as disclosed herein, is used for reducing and/or inhibiting intrauterine adhesions, such as following Hysteroscopies for asherman. In certain embodiments, a hydrogel/hydrogel film, as disclosed herein, is used for reducing and/or inhibiting adhesions following Achilles tendon repairs and/or similar tendon repairs. In certain embodiments, a hydrogel/hydrogel film, as disclosed herein, is used for reducing and/or inhibiting scarring following ENT operations, such as sinus surgery. In certain embodiments, a hydrogel/hydrogel film, as disclosed herein, is used as a plug for dura in spinal surgery, for reducing peridural adhesions in spinal surgery, reducing peridural adhesions in carniectomies (neurosurgery), as a healing adjunct in burn injuries, for chemical lesions of oral mucosa, for use in ophthalmology as adjunct for corneal and conjunctival ulcers, for barret's esophagus, gastritis, GERD, for anorectal fistulas, preventing urethral strictures after urological operations, for use in intraperitoneal radiation therapy to prevent adhesions and bowel obstruction, or any combination thereof.

In some embodiments, as disclosed herein, the pre-gel ECM mixture is disposed onto a target tissue as an instillate infusion. In some embodiments, the instillate may have a volume from 5-20 mL. In some embodiments, the instillate may have a volume from 20-60 mL. In some embodiments, the instillate may have a volume of at least 60 mL.

In some embodiments, a low concentration of ECM hydrogels is used to lubricate organs after surgery. In some embodiments, the low concentration of ECM hydrogels is from about 0.3 mg/ml to about 10 mg/ml. In some embodiments, the low concentration of ECM hydrogels is from about 0.5 mg/ml to about 6 mg/ml.

VI. PREPARATION OF ECM DIGEST

Disclosed herein, in some embodiments, is a method for preparing a pre-gel ECM digest ("ECM digest"), as disclosed herein, which forms a hydrogel upon exposure to one or more stimuli and reduces and/or inhibits tissue adhesion on a target tissue. In some embodiments, the ECM digest comprises any type of mammalian ECM. In some embodiments, the mammalian ECM comprises a collagen to carbohydrate ratio of at least about 70:1. In some embodiments, the mammalian ECM comprises a collagen to carbohydrate ratio from about 50:1 to about 600:1. For example, bone ECM is known to comprise a collagen to carbohydrate ratio of at least about 70:1. In some instances, the bone ECM comprises a collagen to carbohydrate ratio of at least about 100:1. In some embodiments, the ECM digest comprises more than one type of ECM, wherein the ECM digest comprises a collagen to carbohydrate ratio from about 70:1 to about 400:1.

In some embodiments, the desired type(s) of mammalian ECM is obtained from a tissue or at least a portion of an organ, from a mammal, such as pig, cow, sheep, dog, cat, deer, buffalo, elk, goat, and/or human. In a non-limiting example, bone ECM is obtained from bone material of a mammal. In some embodiments, the bone material comprises cancellous bone. In another non-limiting example, the bone material comprises cancellous bone of at least 50% or more by weight. In yet another non-limiting example, the bone material comprises cancellous bone of at least 50%, 60%, 75%, 80%, 90%, 95%, 99%, or greater than 99% by weight of cancellous bone. In some embodiments, the bone material is free or substantially free of cortical bone.

In some embodiments, the ECM tissue is comminuted, e.g., reduced into smaller pieces or particles. In a non-limiting example, bone material is comminuted using available methods, such as by grinding, milling, crushing, chopping, pulverizing, and/or other similar methods.

In some embodiments, the isolated ECM tissue is demineralized using an acid or chelating agent. In some embodiments, an acid used for demineralizing the isolated ECM tissue includes: hydrochloric acid, nitric acid, phosphoric acid, sulfuric acid, boric acid, hydrofluoric acid, hydrobromic acid, perchloric acid, acetic acid, lactic acid, formic acid, citric acid, succinic acid, oxalic acid, uric acid, or any combination thereof. In some embodiments, a chelating agent used for demineralizing the isolated ECM tissue include ethylenediaminetetraacetic acid (EDTA) and salts thereof, such as mono-, di-, tri- and tetra-sodium EDTA, ethylene glycol tetraacetic acid (EGTA), nitrilotriacetic acid (NTA), pentasodium tripolyphosphate (STPP), trisodium carboxymethyloxysuccinate (CMOS), or any combination thereof. Factors such as pH, temperature, fineness of comminution of the ECM tissue, salt content, agitation, and/or concentration of the chelating agent impact the effectiveness of using a chelating agent for demineralizing ECM tissue. In some embodiments, an acid is combined with the chelating agent or salt thereof to demineralize the bone (as discussed further below), depending on the solubility of the chelating agent in the acid. In some embodiments, the demineralized ECM tissue was separated from the acid and rinsed.

In some embodiments, the demineralized ECM tissue is de-lipidized, i.e. lipids are removed from the demineralized ECM tissue. In some embodiments, the demineralized ECM tissue is de-lipidized based on the amount of fat is in the ECM tissue, which varies by the source tissue and species. In some embodiments, de-lipidization of the demineralized ECM tissue occurs through organic extraction using organic solvent(s), provided the desired ECM digest properties and characteristics are not significantly impacted. In some embodiments, organic solvents used for de-lipidization include chloroform, dichloromethane, alcohols such as methanol, ethanol and propanol (including isopropanol and n-propanol), or any combination thereof. In some embodiments, delipidization occurs by incubating the demineralized ECM tissue in chloroform. In some embodiments, the demineralized ECM tissue is incubated with any combination of chloroform and methanol mixed together. For example, the ratio between chloroform and methanol can be 1:1. In some embodiments, the demineralized ECM tissue is incubated for about 0-24 hr. In some embodiments, the demineralized ECM tissue is incubated for greater than 24 hr. In some embodiments, following incubations, the demineralized ECM tissue is washed and/or rinsed. In some embodiments, the demineralized ECM tissue is washed with an alcohol, such as methanol, and then subsequently washed with an aqueous solvent, such as water, saline or PBS. In some embodiments, following being washed and/or rinsed, the demineralized ECM tissue is snap frozen and lyophilized. In some embodiments, demineralized ECM tissue is stored at a temperature below 0° C. In some embodiments, demineralized ECM tissue is stored at a temperature of about −20° C. or below.

In some embodiments, as disclosed herein, demineralized EMC tissue and/or de-lipidized EMC tissue are decellularized through incubation in one or more decellularization agents to remove cells from the demineralized ECM tissue. In some embodiments, demineralized ECM tissue that was previously lyophilized is rinsed with water, such as distilled water, prior to being mixed with decellularization agents. In some embodiments, decellularization of the demineralized ECM tissue is performed using one or more enzymes, such as proteases. In some embodiments, the demineralized ECM tissue is incubated with a protease for at most 72 hours. In some embodiments, the demineralized ECM tissue is incubated with a protease for about 12-48 hours. In some embodiments, the demineralized ECM tissue is incubated with a protease for about 24 hours. In some embodiments, the protease is trypsin. In some embodiments, in a non-limiting example, the trypsin concentration is about 0.05%. In some embodiments, decellularization of the demineralized ECM tissue occurs between 20-37° C. In some embodiments, the demineralized ECM tissue is incubated with a chelating agent as well as the protease. In some embodiments, the chelating agent is EDTA. In some embodiments, in a non-limiting example, the chelating agent is provided at a concentration of 0.02%. In some embodiments, decellularization is performed through exposure to hypertonic saline, peracetic acid, Triton-X and/or other detergents.

In some embodiments, the decellularized ECM tissue is washed to remove protease and chelating agent, if present, as well as remaining cellular material(s). In some embodiments, the decellularized ECM tissue is washed in an aqueous solvent such as water, saline or PBS at any concentration. The aqueous solvent may be supplemented with additional agents, for example antibiotics. In some embodiments, the antibiotics are penicillin and/or streptomycin. This rinse may occur under any suitable conditions known to those of skill in the art, so long as functionality of the matrix in its ability to gel when the temperature is raised to approximately 37° C., and to support cell growth. In some embodiments, the decellularized ECM tissue is rinsed for at least 12 hours, at a temperature of less than about 15° C. In some embodiments, the decellularized ECM tissue is rinsed at 4° C. In some embodiments, the decellularized ECM tissue is snap frozen and lyophilized to form a solid, and stored at a temperature below 0° C. In some embodiments, the lyophilized decellularized ECM tissue is stored at about −20° C. or less.

In some embodiments, digesting and solubilizing the decellularized ECM tissue forms an ECM digest. In some embodiments, the decellularized ECM tissue is digested and solubilized by using of an acid protease. In some embodiments, the use of the acid at a prescribed concentration enables for pH adjustment of the decellularized ECM solution (decellularized ECM tissue, acid, and acid protease), thereby enabling for optimal activation of the protease and solubilization of the decellularized ECM material. In some embodiments, the acid protease is pepsin, and the acid used is hydrochloric acid. In some embodiments, the acid protease is trypsin. In some embodiments, the acid used is acetic acid. In some embodiments, the decellularized ECM solution is agitated for at least 72 hours. In some embodiments, the decellularized ECM solution is agitated for at least 96 hours. In some embodiments, the resulting pre-gel ECM digest is stored at a temperature below 0° C. In some embodiments, the pre-gel ECM digest is stored at about −20° C. or less.

In some embodiments, the pre-gel ECM digest, decellularized ECM tissue, and/or demineralized ECM tissue are sterilized. In some embodiments, sterilization techniques include glutaraldehyde tanning with glutaraldehyde, formaldehyde tanning at acidic pH, ethylene oxide treatment, propylene oxide treatment, gas plasma sterilization, gamma radiation, electron beam and/or peracetic acid sterilization. In some embodiments, a sterilization technique which does not significantly affect the characteristics of the ECM tissue is used. In some embodiments, the sterilization technique comprises exposing the ECM material (e.g., pre-gel ECM digest) to peracetic acid, 1-4 Mrads gamma irradiation, and gas plasma sterilization.

In some embodiments, prepared ECM digest is stored for future use to reduce and/or inhibit post-surgical tissue adhesion, as disclosed herein. In some embodiments, the ECM digest is lyophilized and formed into a powder. As disclosed herein, the lyophilized ECM digest powder can be reconstituted by mixing with distilled water, a buffer solution, an aqueous solution, and so on. In some embodiments, the prepared ECM digest is suspended in a solution at a temperature less than or equal to 4° C.

In some embodiments, the ECM digest is neutralized by being mixed with a buffer solution. In some embodiments, the pH of the ECM digest is neutralized by adding a base, such as sodium hydroxide (NaOH) to the ECM digest. In some embodiments, the ECM digest is neutralized to provide a solution that has a pH between about 7 and about 8. In some embodiments, the ECM digest is neutralized to provide a solution that has a pH between about 7.2 and 7.8. In some embodiments, the ECM digest is neutralized to provide a solution that has a pH of about 7.4. In some embodiments, the ECM digest is neutralized by being mixed with 0.1 N NaOH in 10×PBS, followed by dilution with 1×PBS.

VII. EXAMPLES

The following examples are included for illustrative purposes only and are not intended to limit the scope of the invention.

Example 1: Administering Neutralized ECM Digest onto Test Subject

A pre-gel ECM mixture was prepared by mixing an ECM digest with a buffer solution. The pre-gel ECM mixture was then transferred to a syringe, and kept at about 4° C. until ready to be used, wherein the syringe is kept on ice. Ischemic buttons (IBs) on mice were created. Specifically, mice were anaesthetized with inhaled isoflurane during surgery. An anterior midline incision was made through the abdominal wall and peritoneum using a scalpel. Three ischemic buttons (IBs), spaced 1 cm apart, were created on the left side of the peritoneum by grasping 3 mm of the parietal tissue with a hemostat and ligating the base of each segment with 4-0 sutures. Also, the caecum was isolated and rubbed gently with sterile cotton swabs to produce an injury in the visceral peritoneum.

After preparing the IBs, the syringe was attached with an atomizer, such as LMA Nasal Mucosal Atomization device (by Teleflex Medical), which was used to spray the pre-gel ECM mixture onto the aforementioned affected peritoneal tissue of the mice, wherein the pre-gel ECM mixture was reduced by the atomizer to droplets or particles having a maximum diameter of 250 μm. The pre-gel ECM mixture is sprayed onto the affected tissue to apply a uniform 1-2 mm film coating. The temperature of the tissue and environment surrounding the tissue caused gelation of the pre-gel ECM mixture to form a hydrogel film of less than 2 mm disposed over affected tissue. The hydrogel film provided a barrier over the affected tissue to prevent adhesion formation with adjacent tissues in the mice.

Example 2: Comparison of Hydrogel Retention Based on Pre-Gel ECM Mixture Droplet Size The experiment methodology as described in Example 2 was used to compare the retention of a hydrogel film on a target tissue based on size of the pre-gel ECM mixture droplet that was sprayed onto to the target tissue. Specifically, the pre-gel ECM mixture, using bone ECM, was disposed onto a target tissue of a first set of mice using via a 25 G needle, wherein the inner diameter of the needle is 250 µm, thereby reducing the pre-gel ECM mixture into droplets (or particles) having an average diameter less than 250 µm. The pre-gel ECM mixture was also sprayed onto a second set of mice using a syringe and attached atomizer, wherein the pre-gel ECM mixture was reduced to droplets having a diameter of 30-100 µm. The pre-gel ECM mixture in both sets were covalently labeled with a fluorescent tag.

Figure 1B:
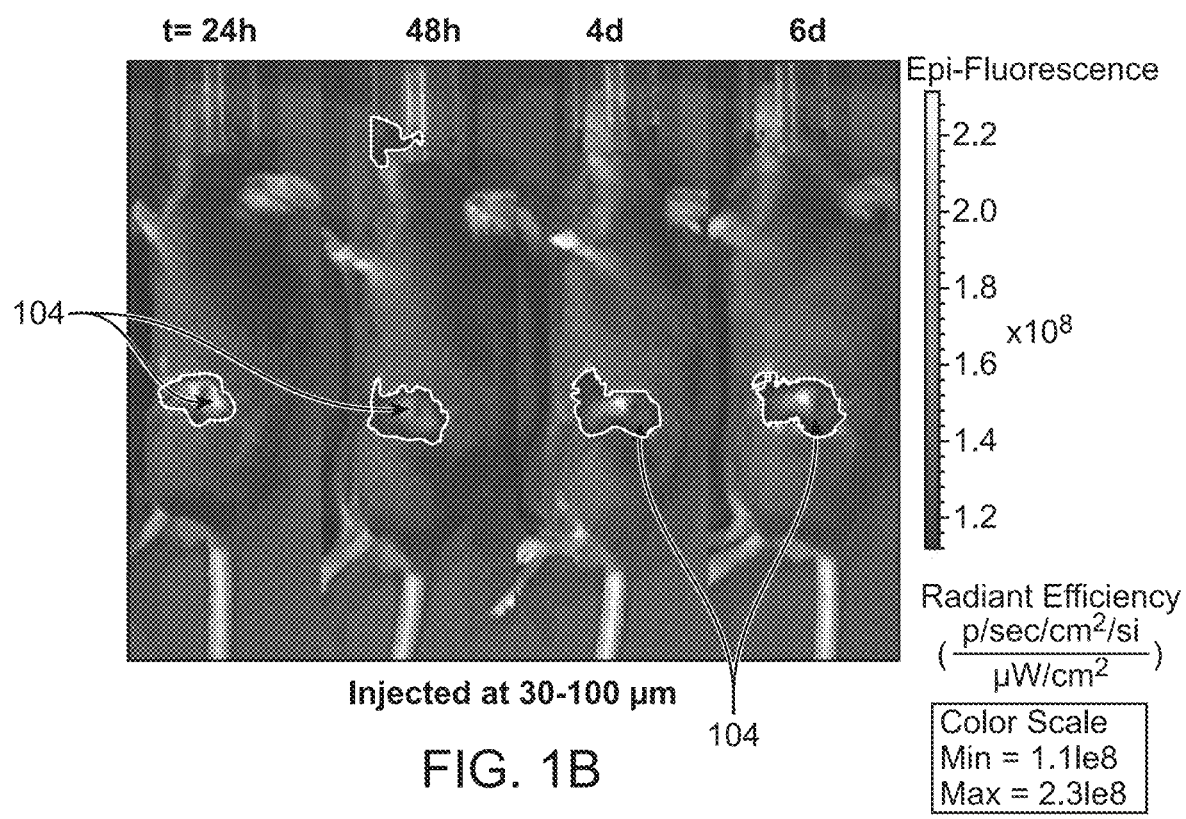
FIG. 1B depicts an image of hydrogel film retention on peritoneal issue over 6 days, wherein the hydrogel film was formed from ECM mixture particles having a diameter between 30-100 µm.

FIGS. 1A-1B depict images of fluorescently labelled hydrogel film formed from the gelled pre-gel ECM mixtures, and the hydrogel film adherence over time for the pre-gel ECM mixture having droplet sizes on average of less than 250 µm (FIG. 1A, reference character 102) and on average between 30-100 µm (FIG. 1B, reference character 104). As depicted in FIG. 1A, the detectable hydrogel film 102 in the peritoneal cavity of the subject mouse, as measured using fluorescent labeling, reduced significantly after 48 hours, thereby suggesting the hydrogel film 102 failed to remain adhered to the target tissue after 2 days of being disposed thereon. By contrast, as depicted in FIG. 1B, the detectable hydrogel film 104 in the peritoneal cavity of the subject mouse, as measured using fluorescent labeling, was detectable after 144 hours (6 days), thereby suggesting the hydrogel film 104 remained adhered to the target tissue after 6 days of being disposed thereon. As such, by remaining adhered to the target tissue, the hydrogel film 104 formed from a pre-gel ECM mixture having an average droplet size between 30-100 µm continued to provide a barrier over said target tissue for 6 days so as to help reduce and inhibit adhesion with adjacent tissues.

Example 3: Comparison of Hydrogel Retention Based on Hydrogel Stiffness

The experiment methodology as described in Example 2 was used to evaluate the reduction of post-surgical tissue adhesion with ECM based hydrogel. Specifically, the pre-gel ECM mixture, using bone ECM, was sprayed onto the target tissue of a first set of mice using a syringe and attached atomizer, wherein the pre-gel ECM mixture was reduced to droplets having an average diameter of less than 250 µm. As a comparison, a control comprising a saline solution was sprayed onto target tissue of a second set of mice using a syringe and attached atomizer, wherein the saline solution was reduced to particles having a diameter less than 250 µm.

Figure 2:
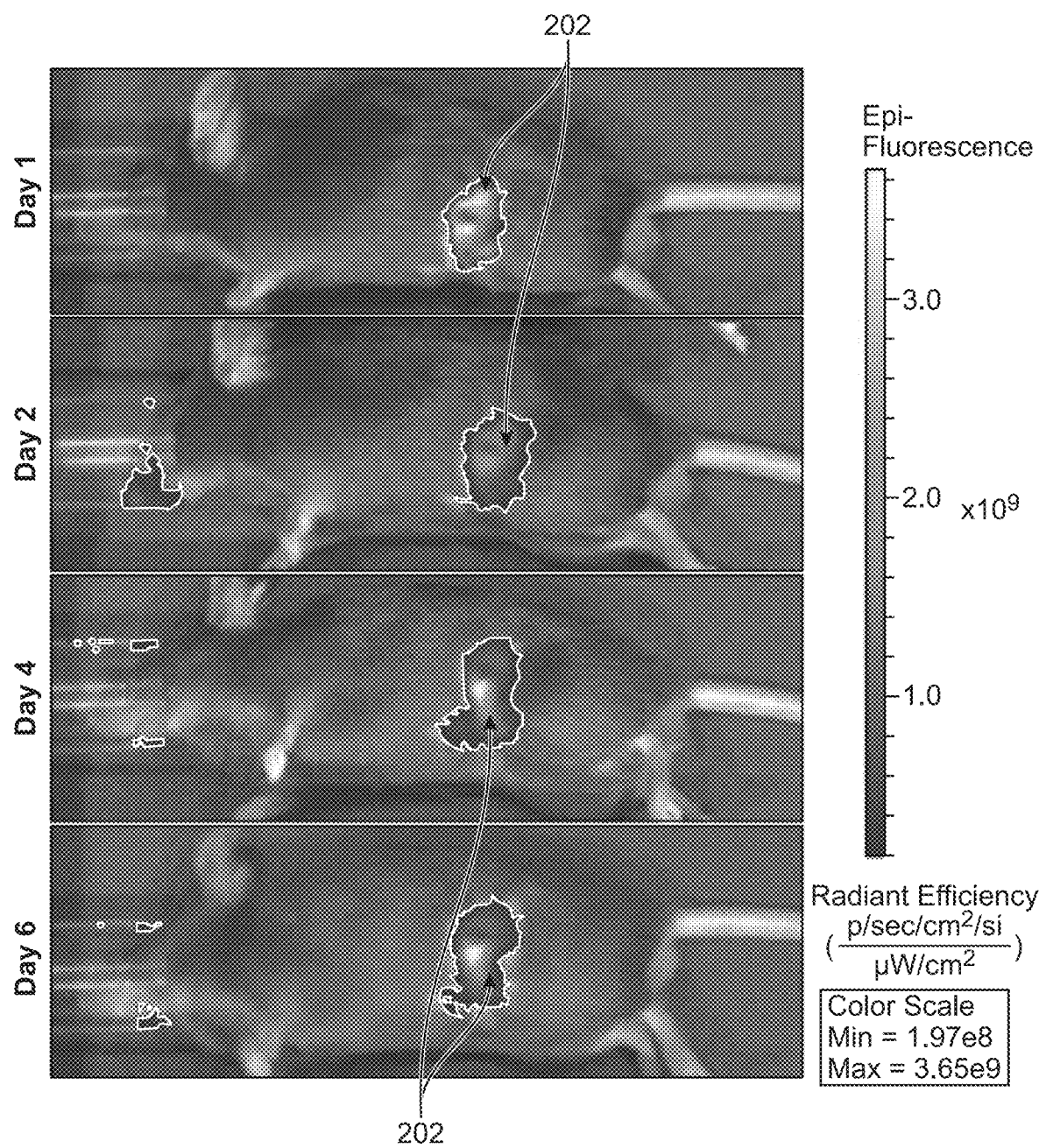
FIG. 2 depicts an image of fluorescently labelled ECM based hydrogel and adherence on a target tissue over time.
Figure 3A:
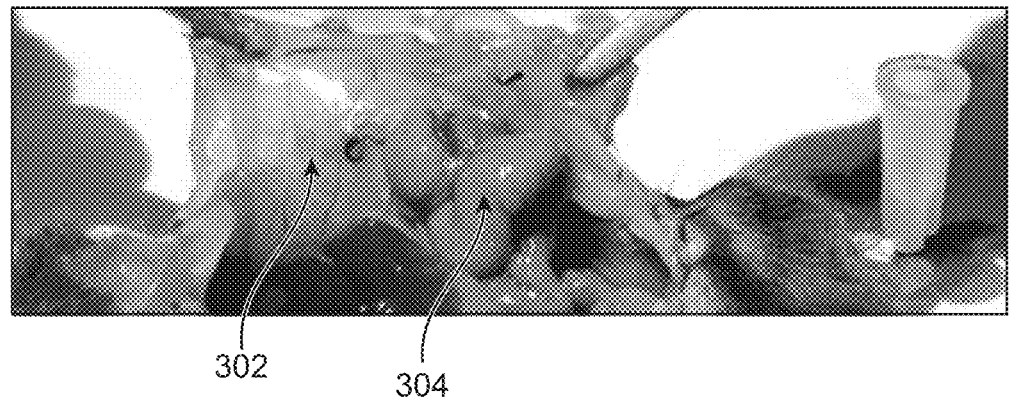
FIGS. 3A-B depicts a representation of a comparison of tissue adhesion between a target tissue and surrounding tissues, wherein the target tissue was disposed with a saline solution (control) (FIG. 3A), and an ECM based hydrogel (ECM spray) (FIG. 3B), after a surgical operation on the target tissue.
Figure 3B:
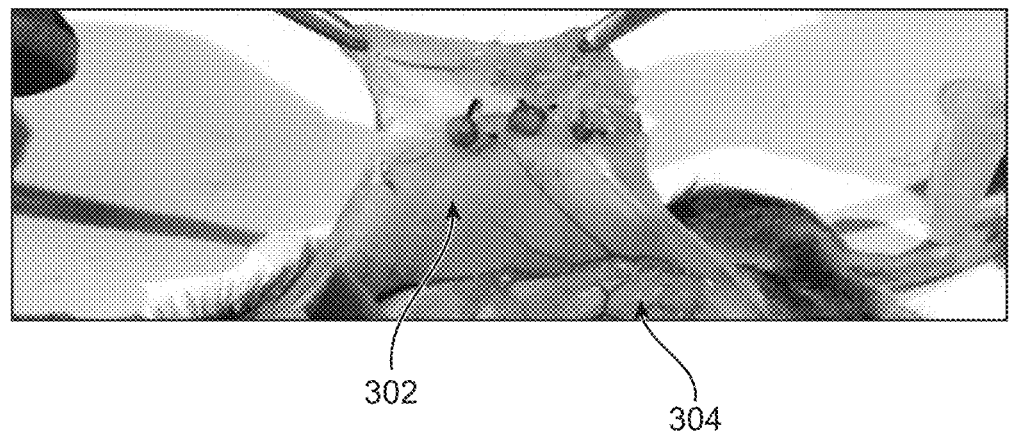
Figure 4:
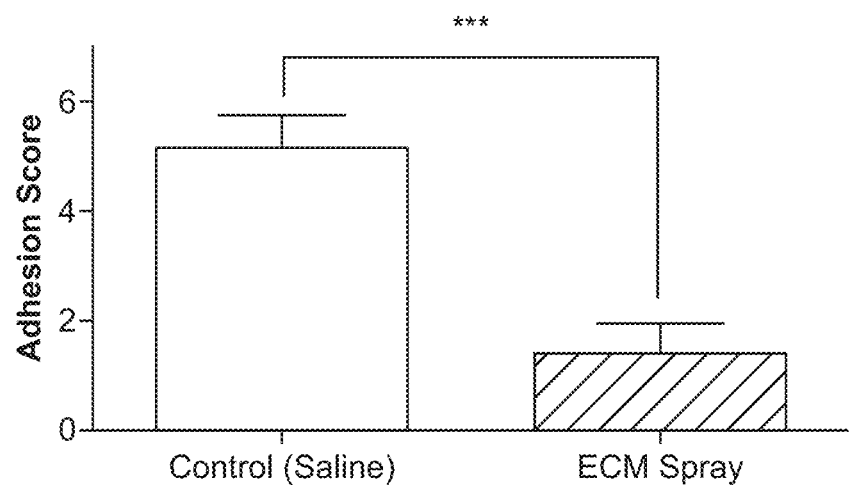
FIG. 4 depicts a representation of a comparison of an adhesion score between using a saline solution (control) and ECM based hydrogel for reducing tissue adhesion.
Figure 5:
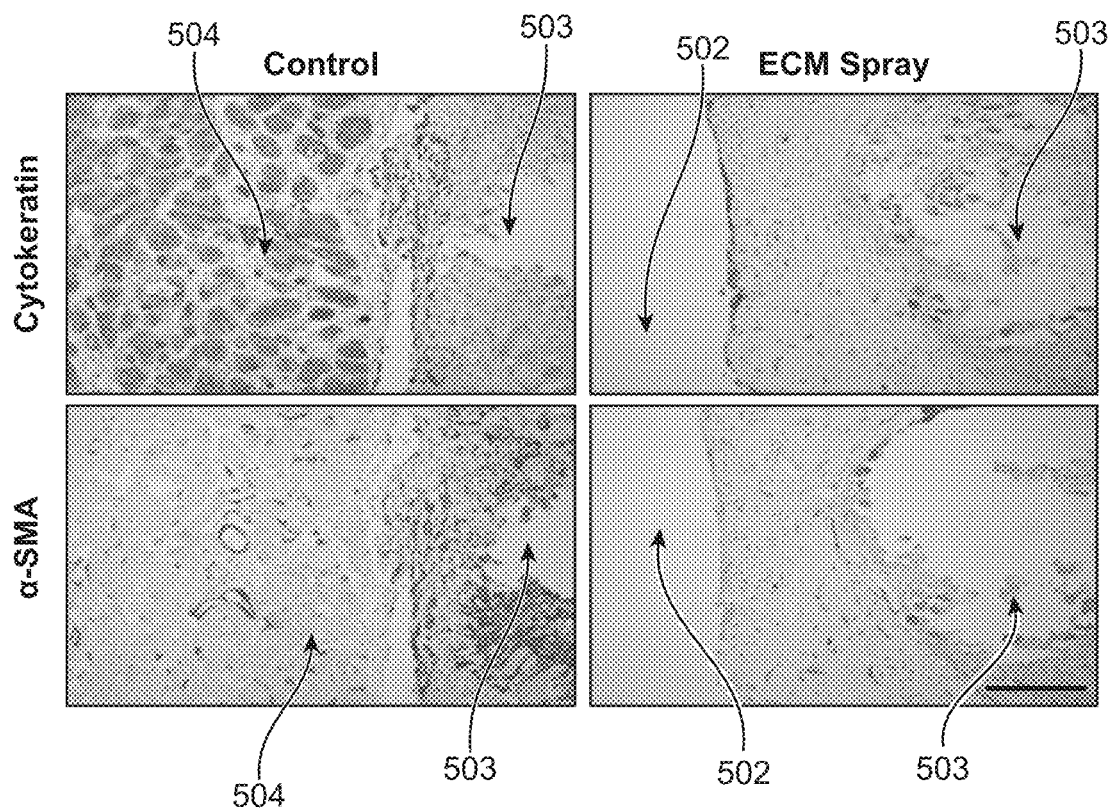
FIG. 5 provides an immunohistochemistry analysis that shows an intact epithelial layer (via cytokeratin staining) after using ECM based hydrogel, whereas the control (saline solution) lacks an epithelial layer and has an increased scarring profile.

The extent and tenacity of adhesions formed were quantified with a standard scoring system. The data showed that the ECM based hydrogel 202 was retained at the surgical site 6+ days after application, as shown in the images showing a fluorescently labelled hydrogel over time (FIG. 2). Accordingly, the ECM based hydrogel resulted in a 75% reduction in the incidence and tenacity of adhesions as compared to the saline control group, as shown in FIGS. 3A-B and 4. For example, FIG. 3A depicts an image of resulting tissue adhesion between an abdominal wall 302 and intestinal tissue 304 following a surgical procedure and after being sprayed with a saline control group, wherein scarring is present between the abdominal wall 302 and intestinal tissue 304. By contrast, FIG. 3B depicts an image showing the absence of tissue adhesion between the abdominal wall 302 and intestinal tissue 304 after being sprayed with the ECM based hydrogel. FIG. 4 provides a comparison of an adhesion score between using a saline control group and ECM based hydrogel, wherein spraying the saline control group onto a tissue following surgical procedure resulted in an adhesion score of about 5, while spraying the ECM based hydrogel onto a tissue following surgical procedure resulted in an adhesion score of about 2. As used herein, an adhesion score refers to a semi-quantitative measure of the surface area covered with tissue adhesion, and strength of the adhesion. In some embodiments, the adhesion score is based on dividing a tissue area by quadrants, and determining how many of the quadrants comprised tissue adhesion and the strength of the corresponding adhesion. Furthermore, FIG. 5 depicts a visual contrast in a tissue environment when using a saline control group and ECM based hydrogel. The reference character 503 refers to a tissue injury site. As noted, the use of a saline control spray resulted in tissue adhesion, as demonstrated with reference character 504, while the use of the ECM spray did not result in tissue adhesion (reference character 502). Moreover, the use of α-SMA provides a marker for secreting scar tissue, which is visible with the dark spots located in 504 of the bottom left square in FIG. 5. The ECM based hydrogel seems to help prevent adhesions but also as a substrate for tissue healing and promoting a predominantly epithelial cell phenotype, while the control group was characteristic by a largely scarring 504 (mesenchymal) phenotype. Stated differently, the application of an ECM based hydrogel to surgically injured tissue resulted in re-epithelialization and reduced scarring (502) compared to the control where surgically injury results in scarring/adhesions (504) at the site of surgical injury in the absence of re-epithelialization.

Example 4: Experiment and Comparison of Multiple Hydrogel Types

Experiments are conducted with ischemic buttons (IBs) created on the peritoneum of mice. The experiments include the following seven experimental groups: 1) Control group, which consists of adding saline over the IBs; 2) Pluronic Spray, for a synthetic hydrogel that has similar gelation profile to ECM hydrogels, wherein Pluronic F127 will be used at 25% w/v; 3) Bone ECM hydrogel spray; 4) ECM hydrogel spray with a physical cross-linker will be used at 25% w/v; 5) ECM hydrogel spray with a chemical cross-linker will be used at 25% w/v; 6) ECM powder is first applied over IBs followed by ECM hydrogel spray; and 7) ECM powder applied over IBs.

For each of the experimental groups, a sample size of 8 mice is used. Moreover, except for the application of ECM powder, the amount of spray for each experimental group will be 400 ul/mouse.

Example 5: Immune Modulation by ECM Hydrogel

Figure 6:
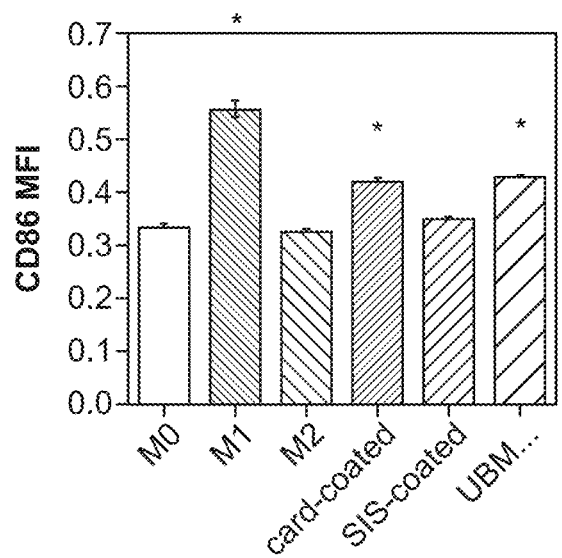
FIG. 6 depicts a representation of an example of anti-inflammatory favorable environment resulting from exposure to ECM from various tissues.

FIG. 6 depicts a non-limiting example of the effect that ECM material has on an M1 pro-inflammatory phenotype, which induces inflammation. The marker CD86 MFI (mean fluorescence intensity) was used as a marker for the M1 pro-inflammatory phenotype. An exemplary cardiac-coated solution, a SIS-coated (small intestinal submucosa) solution, and UBM (urinary bladder matrix) solution were exposed to ECMs from various types of tissues, wherein the level of CD86 were obtained by mean fluorescence intensity (MFI). The control M0, M1 and M2 were provided as a relative gauge. Exposure to the ECMs provided CD86 levels that were lower than the control M1, thereby promoting an anti-inflammatory environment.

Figure 7:
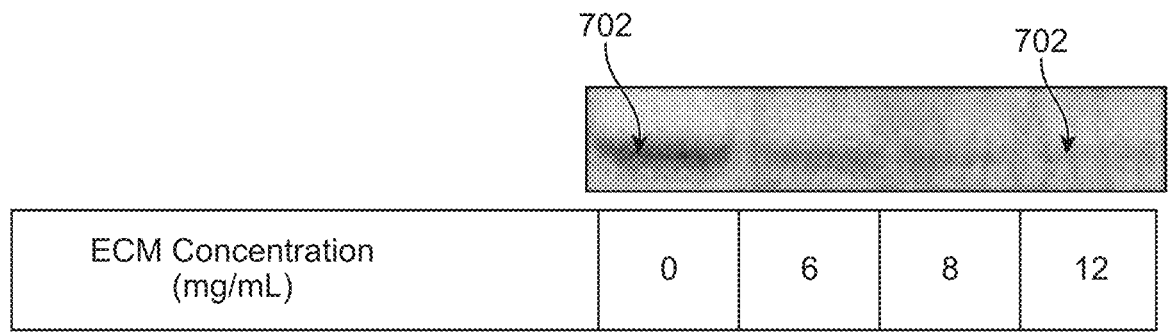
FIG. 7 depicts an image of cells grown on ECM hydrogels that down-regulate matrix metalloproteinase activity as shown by gel zymography.
Figure 8:
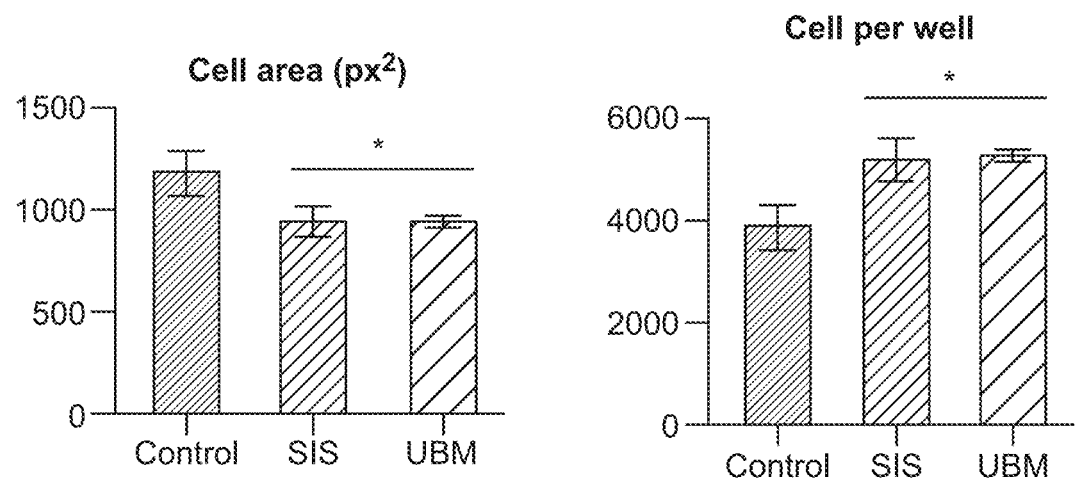
FIG. 8 depicts an image of cells in ECM hydrogels from various tissues (small intestinal submucosa (SIS) and urinary bladder matrix (UBM)) that have reduced TGF-driven EMT.
Figure 9:
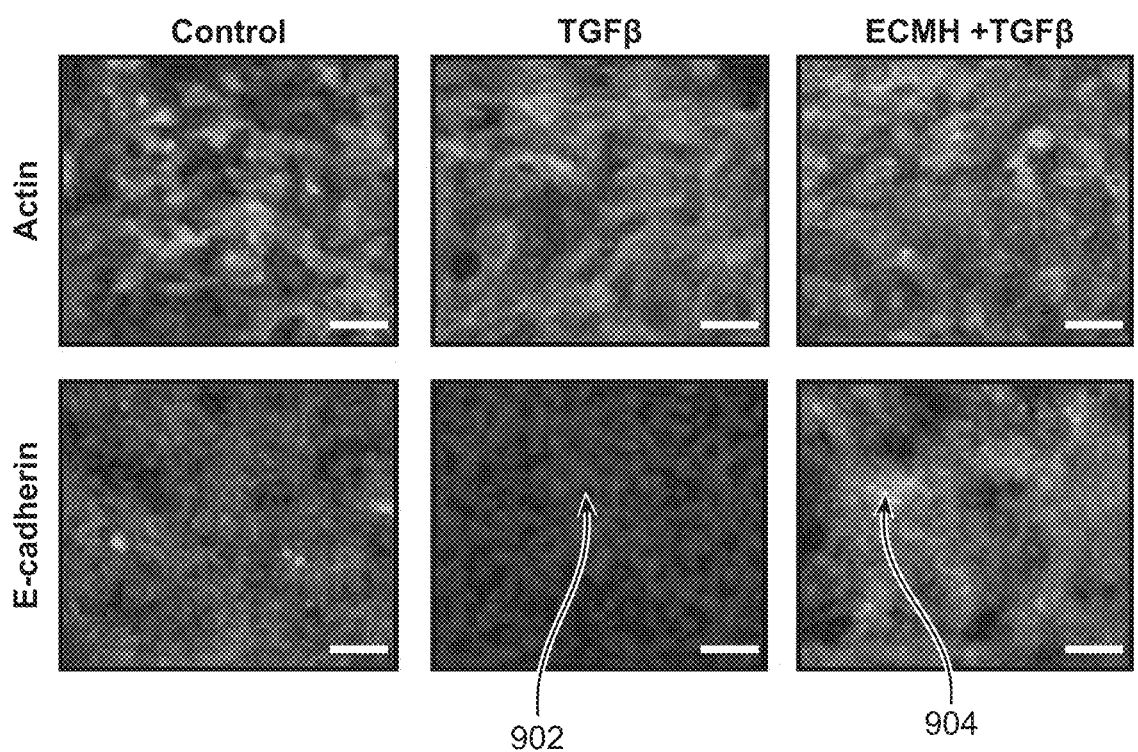
FIG. 9 depicts an image of ECM hydrogels that support the maintenance of epithelial phenotype.

Moreover, FIGS. 7-9 depicts non-limiting examples of ECM material shown to reduce the occurrence of fibrosis by reducing or inhibiting the Epithelial-to-Mesenchymal Transition. For example, FIG. 7 depicts an in-gel zymography image that shows decreasing matrix metalloproteinase activity (reference character 702) in cells as they are exposed to increasing concentrations of ECM. FIG. 8 shows that of cells exposed to ECM hydrogels have lower cell area and increased cell proliferation compared to controls. The data in FIG. 8 suggest that the epithelial/mesothelial phenotype is favored over the mesenchymal phenotype when cells are exposed to ECM hydrogels from various tissues (small intestinal submucosa (SIS) and urinary bladder matrix (UBM)) and have reduced TGF-driven EMT. FIG. 9 depicts images of epithelial cells in various conditions and show that ECM hydrogels support the maintenance of epithelial phenotype in the context of TGF-driven EMT. For example, reference character 902 refers to the loss of epithelial phenotype when cells are only exposed to TGFβ, while reference character 904 refers to the retention of the epithelial phenotype when cells are exposed both ECM and TGFβ.

Example 6: Reduction of Postsurgical Tissue Adhesion in Humans with Use of ECM-Based Hydrogel Postsurgical tissue adhesion in humans is reduced by 50% when spraying a pre-gel ECM over a target tissue after a related target tissue. Upon completion of the surgical procedure, a target tissue for a human patient is sprayed with a pre-gel ECM mixture, as described herein, for example in the section "Method for reducing postsurgical tissue adhesion with ECM based hydrogel". The pre-gel ECM mixture comprises a bone ECM digest combined with a buffer solution. The pre-gel ECM mixture is at room temperature (about 22° C.). The ECM digest has a collagen to carbohydrate ratio from about 70:1 to about 400:1. By combining the buffer solution with the ECM digest, the pre-gel ECM mixture has a pH of around 7, which promotes a phase change of the pre-gel ECM to form a hydrogel. The pre-gel ECM mixture is sprayed as a plurality of particles and forms a coating over the targeted tissue. The temperature of the target tissue is about human body temperature (about 37° C.), wherein the higher temperature of the target tissue than the pre-gel mixture further promotes gelation of the pre-gel mixture into a hydrogel. The pre-gel mixture coating over the target tissue forms a hydrogel film having a thickness of at least 5 μm. The storage modulus of the hydrogel film is at least 100 Pa. The opening to the first human patient (enabling access to the target tissue) is closed, and the first human patient is monitored. The pre-gel mixture is further provided with a fluorescent tag to enable such monitoring.

For a second human patient, a saline control solution (PBS) is sprayed onto a target tissue following a surgical procedure. The opening to the second human patient (enabling access to the target tissue) is closed, and the second human patient is monitored. The saline control solution is further provided with a fluorescent tag to enable such monitoring.

Based on the fluorescence or contrast agent measurement, it is observed saline control solution did not last more than a day on the target tissue. As a result, tissue adhesion and scarring occurred for the second human patient. By contrast, based on the fluorescent, contrast agent, or direct visual measurement, the hydrogel film remained on the target tissue of the first human patient for at least 3 days. As a result, there is around 50% or less tissue adhesion and scarring observed as compared to when using the saline control solution.

Example 7—Measurement of Pre-Gel ECM Mixture Particle Size

As described herein, a pre-gel ECM mixture is applied to a target tissue as a plurality of particles having of size wherein the average maximum dimension of the plurality of particles is at most about 500 μm. The size of the particles may be measured by parallel plate rheometry after gelation occurs with isothermic testing (37° C.) at a steady and constant shear strain γ=1% and f=1.6 Hz.

Example 8—Measurement of Hydrogel and Hydrogel Film Storage Modulus

As described herein, a pre-gel ECM mixture is applied to a target tissue and gels to form a hydrogel. The storage modulus of the hydrogel (and resulting hydrogel film over a target tissue) is at least 100 Pa. The storage modulus of the hydrogel is measured by parallel plate rheometry after gelation occurs with isothermic testing (37° C.) at a steady and constant shear strain γ=1% and f=1.6 Hz.

Example 9—Measurement of Shear Stress to Reduce Viscosity of Pre-Gel ECM Mixture As described herein, a pre-gel ECM mixture exhibits at least a 10× reduction in viscosity when shear rate is applied. At an applied shear rate of less than 0.1 $s^{-1}$, the viscosity is at least 1,000 cP. At an applied shear rate of 1,000 $s^{-1}$, the viscosity reduces to no more than 100 cP. In another example, at an applied shear rate of about 0.01 $s^{-1}$, the viscosity is about 800,000 cP, while at an applied shear rate of 5,000 $s^{-1}$, the viscosity reduces to about 8 cP. The shear rate is applied and corresponding viscosity is measured by a parallel plate rheometer at 24° C. FIG. 10, as described herein, provides an exemplary change in viscosity of a pre-gel ECM mixture to change in shear rate.

Example 10—Measurement of Mass Content of Glycosaminoglycans and Collagen in ECM Digest As described herein, the pre-gel ECM mixture comprises an ECM digest having a prescribed range of a collagen to carbohydrate ratio. As described herein, the ratio of collagen to carbohydrate is by mass. In some embodiments, the carbohydrate comprises glycosaminoglycans. The total mass content of collagen in an ECM digest sample can be measured using a commercial kit (e.g., Sircol dye binding assay). The total mass content of glycosaminoglycans in an ECM digest sample can be measured following proteinase K digestion, using a commercial kit (e.g., Blyscan dye binding assay).

Example 11—Retention of ECM Based Hydrogel on Tissue with ECM Having Collagen to Carbohydrate Ratio of at Least 100:1

In another exemplary case, a pre-gel mixture comprising an ECM digest having a collagen to glycosaminoglycans ratio (by mass) of at least 100:1 was sprayed over a target tissue on mice as a plurality of droplets having an average maximum dimension of at most 500 pin. The resulting ECM based hydrogel that formed over the target tissue was observed to adhere to the target tissue, and was retained on the target tissue for at least 6 days, resulting in a reduction in tissue adhesion of at least 70-75% (as compared to spraying the target tissue with a saline control).

Exemplary Embodiments for Methods, Compositions, and Devices for Reducing Post-Surgical Tissue Adhesion and/or Scarring Disclosed herein, in some embodiments, is a method for reducing postsurgical tissue adhesion, the method comprising: disposing a pre-gel extracellular matrix (ECM) mixture onto a target tissue, wherein the pre-gel ECM mixture comprises a plurality of particles each having a maximum dimension of about 250 μm or less, the pre-gel ECM mixture comprising an ECM digest having a collagen to carbohydrate ratio of at least about 70:1, wherein the target tissue and/or environment about the target tissue causes gelation of the pre-gel ECM mixture to form a hydrogel film having a storage modulus of at least about 250 Pa.

Disclosed herein, in some embodiments, is a method for reducing postsurgical tissue adhesion, the method comprising: disposing a pre-gel ECM mixture onto a target tissue, wherein the pre-gel ECM mixture comprises a plurality of particles each having a maximum dimension of about 250 μm or less, the pre-gel ECM mixture comprising an extracellular matrix (ECM) digest, wherein the target tissue and/or environment about the target tissue causes gelation of the pre-gel ECM mixture to form a hydrogel film having a storage modulus of at least about 250 Pa.

Disclosed herein, in some embodiments, is a method for reducing postsurgical tissue adhesion, the method comprising: disposing a pre-gel ECM mixture onto a target tissue, wherein the pre-gel ECM mixture comprises a plurality of particles each having a maximum dimension of about 250 μm or less, the pre-gel ECM mixture comprising an extracellular matrix (ECM) digest having a collagen to carbohydrate ratio of at least about 70:1, wherein the target tissue and/or environment about the target tissue causes gelation of the pre-gel ECM mixture to form a hydrogel film.

Disclosed herein, in some embodiments, is a method for reducing postsurgical tissue adhesion, the method comprising: a) forming a pre-gel ECM mixture comprising a plurality of particles each having a maximum dimension of about 250 μm, the pre-gel ECM mixture comprising an extracellular matrix (ECM) digest having a collagen to carbohydrate ratio of at least about 70:1; and b) disposing the pre-gel ECM mixture onto a target tissue, wherein the target tissue and/or environment about the target tissue causes gelation of the pre-gel ECM mixture to form a hydrogel film having a storage modulus of at least about 250 Pa.

Disclosed herein, in some embodiments, is a method for reducing postsurgical tissue adhesion, the method comprising: a) forming a pre-gel ECM mixture comprising a plurality of particles each having a maximum dimension of about 250 μm, the pre-gel ECM mixture comprising an extracellular matrix (ECM) digest having a collagen to carbohydrate ratio of at least about 70:1; and b) disposing the pre-gel ECM mixture onto a target tissue, wherein the target tissue and/or environment about the target tissue causes gelation of the pre-gel ECM mixture to form a hydrogel film.

Disclosed herein, in some embodiments, is a method for reducing postsurgical tissue adhesion, the method comprising: a) forming a pre-gel ECM mixture comprising a particles each having a maximum dimension of about 250 μm, the pre-gel ECM mixture comprising an extracellular matrix (ECM) digest; and b) disposing the pre-gel ECM mixture onto a target tissue, wherein the target tissue and/or environment about the target tissue causes gelation of the pre-gel ECM mixture to form a hydrogel film having a storage modulus of at least about 250 Pa.

In some embodiments, in any method disclosed herein, disposing the pre-gel mixture comprises spraying the pre-gel mixture onto the target tissue. In some embodiments, in any method disclosed herein, the pre-gel mixture is sprayed uniformly onto the target tissue. In some embodiments, in any method disclosed herein, the hydrogel film covers at least a portion of the target tissue. In some embodiments, in any method disclosed herein, the hydrogel film is configured to adhere to the target tissue upon gelation. In some embodiments, in any method disclosed herein, at least one of the plurality of particles have a maximum dimension of about 100 μm. In some embodiments, in any method disclosed herein, at least one of the plurality of particles have a maximum dimension of about 30-100 μm. In some embodiments, in any method disclosed herein, the hydrogel film has a storage modulus of at least about 500 Pa. In some embodiments, in any method disclosed herein, the hydrogel film has a storage modulus of at least about 1000 Pa. In some embodiments, in any method disclosed herein, the hydrogel film has a thickness of at least about 1 mm. In some embodiments, in any method disclosed herein, the hydrogel film has a thickness from about 30 μm to about 2 mm. In some embodiments, in any method disclosed herein, the ECM digest comprises bone ECM. In some embodiments, in any method disclosed herein, the hydrogel film is configured to substantially or completely degrade at least 6 days after being formed. In some embodiments, in any method disclosed herein, the hydrogel film is configured to substantially or completely degrade at least 7 days after being formed. In some embodiments, in any method disclosed herein, the hydrogel film is configured to adhere to the target tissue for at least 6 days after being formed. In some embodiments, in any method disclosed herein, the hydrogel film is configured to adhere to the target tissue for at least 7 days after being formed. In some embodiments, in any method disclosed herein the target tissue and/or environment surrounding the target tissue causes gelation of the pre-gel ECM mixture less than 5 seconds after being disposed onto the target tissue. In some embodiments, in any method disclosed herein, the target tissue and/or environment surrounding the target tissue provides one or more stimuli to cause gelation of the pre-gel mixture. In some embodiments, in any method disclosed herein, the stimuli is a temperature of at least about 35 degrees C. In some embodiments, in any method disclosed herein, the method further comprising exposing light onto the pre-gel ECM mixture disposed onto the target tissue, wherein the pre-gel ECM mixture comprises a photo-initiator, photosensitizer, and/or light-reactive polymer, so as to cause gelation of the pre-gel mixture upon exposure to said light. In some embodiments, in any method disclosed herein, the pre-gel ECM mixture is disposed onto the target tissue using a device located a prescribed distance from the target tissue. In some embodiments, in any method disclosed herein, the pre-gel ECM mixture is disposed onto the target tissue once a prescribed time after completion of a surgical procedure has lapsed. In some embodiments, in any method disclosed herein, the target tissue is peritoneal, abdominal, pelvic, spinal, orthopedic, nasal, or any combination thereof. In some embodiments, in any method disclosed herein, the plurality of particles is a plurality of droplets. In some embodiments, in any method disclosed herein, the maximum dimension is a maximum diameter.

Disclosed herein, in some embodiments, is a spray particle for reducing postsurgical tissue adhesion, the spray particle having a maximum dimension of about 250 µm or less and comprising: a pre-gel ECM mixture comprising an extracellular matrix (ECM) digest having a collagen to carbohydrate ratio of at least about 70:1, wherein the pre-gel ECM mixture is configured to gel upon being disposed onto a target tissue to form a hydrogel, the hydrogel having a storage modulus of at least about 250 Pa.

Disclosed herein, in some embodiments, is a spray particle for reducing postsurgical tissue adhesion, the spray particle having a maximum dimension of about 250 µm or less and comprising: a pre-gel mixture comprising an extracellular matrix (ECM), wherein the pre-gel mixture is configured to gel upon being disposed onto a target tissue to form a hydrogel, the hydrogel having a storage modulus of at least about 250 Pa.

Disclosed herein, in some embodiments, is a spray particle for reducing postsurgical tissue adhesion, the spray particle having a maximum dimension of about 250 µm or less and comprising: a pre-gel ECM mixture comprising an extracellular matrix (ECM) digest having a collagen to carbohydrate ratio of at least about 70:1, wherein the pre-gel ECM mixture is configured to gel upon being disposed onto a target tissue to form a hydrogel.

In some embodiments, for any spray particle herein, the spray particle has a maximum dimension of about 100 µm. In some embodiments, for any spray particle herein, the spray particle has a maximum dimension of about 30-100 µm. In some embodiments, for any spray particle herein, the hydrogel has a storage modulus of at least about 500 Pa. In some embodiments, for any spray particle herein, the hydrogel has a storage modulus of at least about 1000 Pa. In some embodiments, for any spray particle herein, the ECM digest comprises bone ECM. In some embodiments, for any spray particle herein, the spray particle is a droplet. In some embodiments, for any spray particle herein, the maximum dimension is a diameter.

Disclosed herein, in some embodiments, is a hydrogel film for reducing postsurgical tissue adhesion, the hydrogel film comprising: a coating of gelled pre-gel ECM mixture disposed onto a target tissue, the pre-gel ECM mixture comprising an extracellular matrix (ECM) digest having a collagen to carbohydrate ratio of at least about 70:1, the hydrogel film having a storage modulus of at least about 250 Pa, the hydrogel film having a thickness less than 2 mm, the hydrogel film configured to adhere to the target tissue for at least about 5 days.

Disclosed herein, in some embodiments, is a hydrogel film for reducing postsurgical tissue adhesion, the hydrogel film comprising: an extracellular matrix (ECM) having a collagen to carbohydrate ratio of at least about 70:1, the hydrogel film having a storage modulus of at least about 250 Pa, the hydrogel film having a thickness of less than 2 mm, the hydrogel film configured to adhere to a target tissue for at least about 5 days.

Disclosed herein, in some embodiments, is a hydrogel film for reducing postsurgical tissue adhesion, the hydrogel film formed from any method as disclosed herein, the hydrogel film having a thickness less than 2 mm, the hydrogel film configured to adhere to the target tissue for at least about 5 days.

In some embodiments, for any hydrogel film herein, the hydrogel film covers at least a portion of the target tissue. In some embodiments, for any hydrogel film herein, the hydrogel film has a storage modulus of at least about 500 Pa. In some embodiments, for any hydrogel film herein, the hydrogel film has a storage modulus of at least about 1000 Pa. In some embodiments, for any hydrogel film herein, the hydrogel film has a thickness of at least about 1 mm. In some embodiments, for any hydrogel film herein, the hydrogel film has a thickness of about 30 µm to about 2 mm. In some embodiments, for any hydrogel film herein, the ECM digest comprises bone ECM.

Disclosed herein, in some embodiments, is a device for reducing postsurgical tissue adhesion; the device comprising: a) a pre-gel ECM mixture comprising an extracellular matrix (ECM) digest having a collagen to carbohydrate ratio of at least about 70:1; and b) a device body containing the pre-gel ECM mixture, the body configured to dispose the pre-gel ECM mixture onto a target tissue as a plurality of particles, wherein each particle has a maximum dimension of about 250 µm, wherein the target tissue and/or environment about the target tissue causes gelation of the pre-gel ECM mixture to form a hydrogel film having a storage modulus of at least about 250 Pa.

Disclosed herein, in some embodiments, is a device for reducing postsurgical tissue adhesion; the device comprising: a) a pre-gel mixture comprising an extracellular matrix (ECM); and b) a device body containing the pre-gel ECM mixture, the body configured to dispose the pre-gel ECM mixture onto a targeted tissue as a plurality of particles, wherein each particle has a maximum dimension of about 250 µm, wherein the target tissue and/or environment about the target tissue causes gelation of the pre-gel ECM mixture to form a hydrogel film having a storage modulus of at least about 250 Pa.

Disclosed herein, in some embodiments, is a device for reducing postsurgical tissue adhesion; the device comprising: a) a pre-gel ECM mixture comprising an extracellular matrix (ECM) digest having a collagen to carbohydrate ratio of at least about 70:1; and b) a device body containing the pre-gel ECM mixture, the body configured to dispose the pre-gel ECM mixture onto a targeted tissue as a plurality of particles, wherein each particle has a maximum dimension of about 250 µm, wherein the target tissue and/or environment about the target tissue causes gelation of the pre-gel ECM mixture to form a hydrogel film.

In some embodiments, for any device disclosed herein, the device further comprising an attachment configured to couple with the device body, wherein the pre-gel ECM mixture is reduced to the plurality of particles by passing through said attachment. In some embodiments, the attachment is configured to dispose the plurality of particles onto the target tissue. In some embodiments, the attachment is an atomizer. In some embodiments, for any device disclosed herein, the device body is a spray nozzle. In some embodiments, for any device disclosed herein, the device body is a spray catheter. In some embodiments, for any device disclosed herein, the device body is a syringe. In some embodiments, the syringe tip has a maximum inner diameter of about 250 µm. In some embodiments, for any device disclosed herein, the device body comprises an inlet configured to receive the pre-gel ECM mixture, and an outlet configured to deliver the pre-gel ECM mixture. In some embodiments, the device body comprises a channel disposed between the inlet and outlet. In some embodiments, the attachment from claims any device with an attachment, as disclosed herein, is configured to couple to the outlet. In some embodiments, for any device disclosed herein, wherein disposing the pre-gel ECM mixture comprises spraying the pre-gel ECM mixture onto the target tissue. In some embodiments, the device is configured to spray the pre-gel ECM mixture uniformly onto the target tissue. In some embodiments, for any device disclosed herein, the hydrogel film is configured to adhere to the target tissue upon gelation. In some embodiments, for any device disclosed herein, at least one of the plurality of particles have a maximum dimension of about 100 μm. In some embodiments, for any device disclosed herein, at least one of the plurality of particles have a maximum dimension of about 30-100 μm. In some embodiments, for any device disclosed herein, the hydrogel film has a storage modulus of at least about 500 Pa. In some embodiments, for any device disclosed herein, the hydrogel film has a storage modulus of at least about 1000 Pa. In some embodiments, for any device disclosed herein, the hydrogel film has a thickness of at least about 1 mm. In some embodiments, for any device disclosed herein, the hydrogel film has a thickness of about 30 μm to about 2 mm. In some embodiments, for any device disclosed herein, the ECM digest comprises bone ECM. In some embodiments, for any device disclosed herein, the plurality of particles is a plurality of droplets. In some embodiments, for any device disclosed herein, the maximum dimension is a diameter.

Disclosed herein, in some embodiments, is a composition configured to reduce post-operative tissue scarring, wherein the composition comprises a collagen to carbohydrate ratio of at least about 70:1, the composition configured to gel upon being applied to a target tissue, wherein the gelation results from one or more stimuli. In some embodiments, the composition comprises a collagen to carbohydrate ratio from about 70:1 to about 400:1. In some embodiments, the carbohydrate comprises glycosaminoglycans. In some embodiments, the composition is a liquid or semi-liquid prior to gelation. In some embodiments, the collagen to carbohydrate ratio comprises a collagen to glycosaminoglycans ratio. In some embodiments, the composition comprises hyaluronic acid. In some embodiments, the composition comprises pepsin. In some embodiments, the one or more stimuli comprises a minimum temperature, a prescribed pH range, exposure to light, interaction with a chemical, interaction with an enzyme, or a combination thereof. In some embodiments, the one or more stimuli comprises heat exposure. In some embodiments, the one or more stimuli comprises pH change. In some embodiments, the one or more stimuli comprises light. In some embodiments, the one or more stimuli comprises an interaction with a chemical. In some embodiments, the chemical is a cross-linker. In some embodiments, the one or more stimuli comprises an interaction with an enzyme. In some embodiments, the combination of stimuli comprises heat exposure and pH change. In some embodiments, the thermal stimulus is at least 30° C. In some embodiments, the pH no greater than 7. In some embodiments, the combination of stimuli comprises exposure to a light and interaction with a chemical. In some embodiments, the chemical is a photocross-linker.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for reducing postsurgical scarring at a target tissue, comprising:
   (a) forming particles of a pre-gel mixture, the pre-gel mixture comprising an extracellular matrix (ECM) digest and a buffer solution, wherein the ECM digest comprises a collagen to carbohydrate ratio of at least about 70:1, wherein the buffer solution promotes a phase change of the pre-gel mixture to a hydro gel, wherein the particles of the pre-gel mixture have an average maximum dimension of at most 500 μm;
   (b) applying the particles of the pre-gel mixture to the target tissue at a shear rate of at least 1 $s^{-1}$; and
   (c) promoting the formation of the hydrogel by 1) increasing a temperature of the pre-gel mixture by presenting the pre-gel mixture to the target tissue at a temperature that is lower than a temperature of the target tissue, 2) increasing a temperature of the pre-gel mixture by heating the pre-gel mixture, 3) exposing the pre-gel mixture to a light source; 4) interacting a chemical with the pre-gel mixture; 5) interacting an enzyme with the pre-gel mixture; or 6) a combination thereof, and
   (d) forming a hydrogel film over the target tissue, wherein the hydrogel film is at least 10 μm thick, and comprises a storage modulus of at least 1,000 Pa when measured by parallel plate rheometry after gelation occurs isothermally at 37° C. at constant shear strain of 1% and a frequency of 1.6 Hz,
   wherein the pre-gel mixture is applied onto the target tissue after completion of a surgical procedure,
   wherein the forming of the hydrogel reduces the formation of adhesions on an adjacent tissue.

2. The method of claim 1, wherein applying the pre-gel mixture comprises aerosolizing the pre-gel ECM mixture into particles having an average maximum dimension of less than about 500 μm, less than about 250 μm, or about 30-300 μm.

3. The method of claim 1, wherein applying the pre-gel mixture comprises forming a layer or coating on the target tissue prior to the pre-gel mixture being fully or substantially gelled.

4. The method of claim 1, wherein promoting the formation of a hydrogel comprises forming a single hydrogel film, or a plurality of hydrogel films, which cover an entire surface of the target tissue.

5. The method of claim 1, wherein the hydrogel film has a thickness of at least about 15 μm, or from about 10 μm to about 2 mm.

6. The method of claim 1, wherein the ECM digest comprises bone ECM.

7. The method of claim 1, wherein the hydrogel film is configured to adhere to the target tissue for at least 6 days after being formed, or at least 3 days after being formed.

8. The method of claim 1, wherein promoting the formation of the hydrogel comprise gelation of the pre-gel mixture beginning to occur less than 5 seconds after being applied onto the target tissue.

9. The method of claim 1, wherein promoting the formation of the hydrogel comprises contacting the pre-gel ECM to the target tissue and/or environment surrounding the target tissue, wherein the temperature of the target tissue is at least about 35° C.

10. The method of claim 1, wherein the carbohydrate ratio is from about 70:1 to about 400:1.

11. The method of claim 1, wherein the carbohydrate comprises glycosaminoglycans.

12. The method of claim 1, wherein forming particles of a pre-gel mixture comprises applying shear stress to the pre-gel mixture, wherein the viscosity of the pre-gel mixture is reduced upon being subject to shear stress.

13. The method of claim 12, wherein the viscosity of the pre-gel mixtures is reduced from about 1,000 cP to about 100 cP, when increasing an applied shear rate on the pre-gel mixture from about 0.1 s−1 to about 1,000 s−1.

14. The method of claim 1, wherein the target tissue is intestinal, endometrium, peritoneal, abdominal, pelvic tissue, or any combination thereof.

15. The method of claim 14, wherein the forming of the hydro gel increases expression of an epithelial cell phenotype on the target tissue.

16. The method of claim 14, wherein the forming of the hydrogel reduces expression of a mesenchymal cell phenotype on the target tissue.

17. The method of claim 14, wherein the forming of the hydrogel reduces the formation of fibrosis, or scar tissue on the target tissue or an adjacent tissue.

\* \* \* \* \*